(12) United States Patent
Kaga

(10) Patent No.: US 6,468,223 B2
(45) Date of Patent: Oct. 22, 2002

(54) METHOD AND APPARATUS FOR PREDICTING AND DETECTING OVULATION

(76) Inventor: Kamal Kaga, 49 Meer Dr., Langhorne, PA (US) 19053

(*) Notice: Subject to any disclaimer, the term of this patent is extended or adjusted under 35 U.S.C. 154(b) by 24 days.

(21) Appl. No.: 09/781,713

(22) Filed: Feb. 12, 2001

(65) Prior Publication Data

US 2002/0111561 A1 Aug. 15, 2002

(51) Int. Cl.$^7$ ............................................. A61B 10/00
(52) U.S. Cl. ......................................................... 600/551
(58) Field of Search .................. 600/551; 204/408, 204/450; 324/94, 425–450

(56) References Cited

U.S. PATENT DOCUMENTS

| 5,108,889 A | * | 4/1992 | Smith .............................. 435/4 |
| 5,813,981 A | * | 9/1998 | Carim ........................... 600/372 |
| 6,120,676 A | * | 9/2000 | Heller et al. .............. 205/777.5 |
| 6,356,779 B1 | * | 3/2002 | Katzenmaier et al. ...... 600/391 |

\* cited by examiner

Primary Examiner—Kevin Shaver
Assistant Examiner—Pamela L Wingood
(74) Attorney, Agent, or Firm—Abelman, Frayne & Schwab

(57) ABSTRACT

An apparatus and method for monitoring, predicting and detecting ovulation during the menstrual cycle of a female subject is based upon daily changes in frequency of an oscillator circuit when a capacitive oral sensor is placed in contact with the subject's saliva. An oral sensor that forms a component in the oscillator circuit contained in a hand-held, portable device includes a pre-programmed integrated circuit device with data processing and control capacities, data storage and display means for measuring, recording and processing historical baseline data and relative frequency changes within the subject's current menstrual cycle.

41 Claims, 13 Drawing Sheets

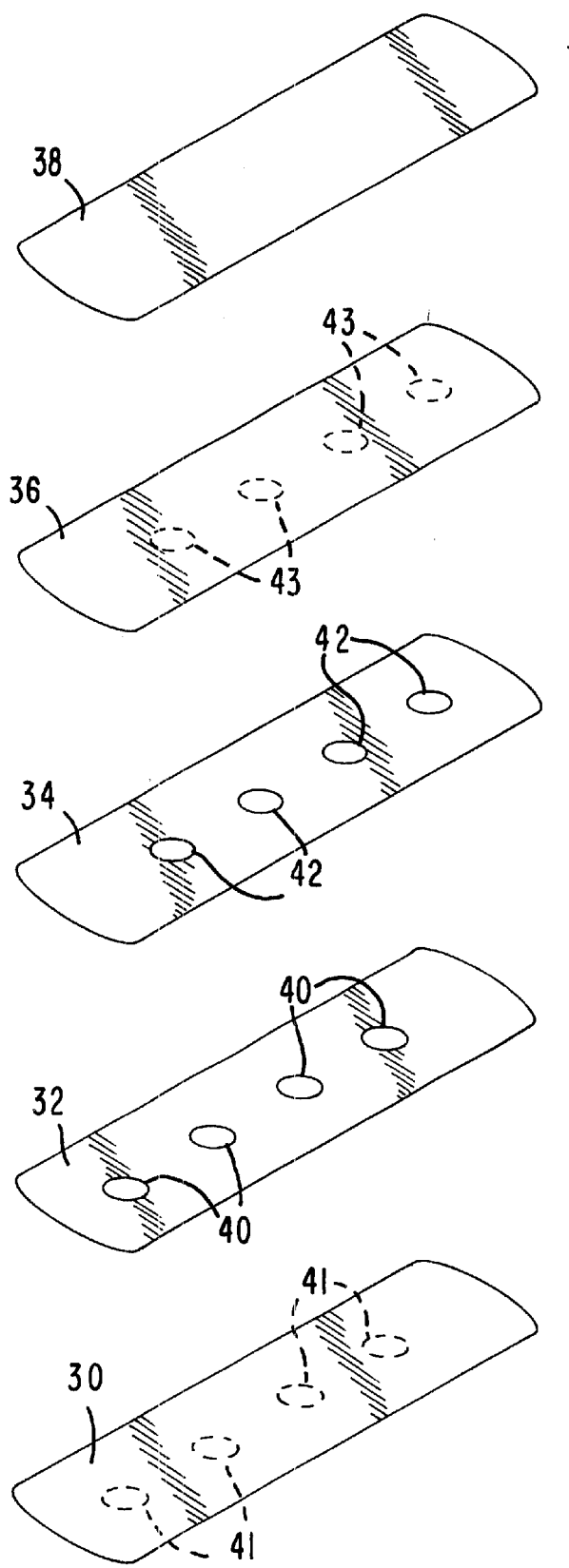

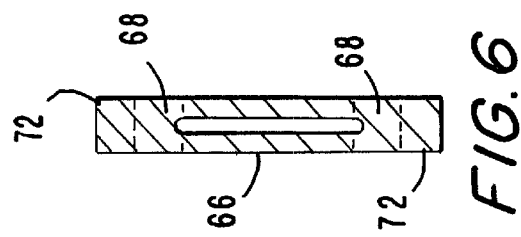
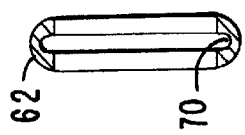
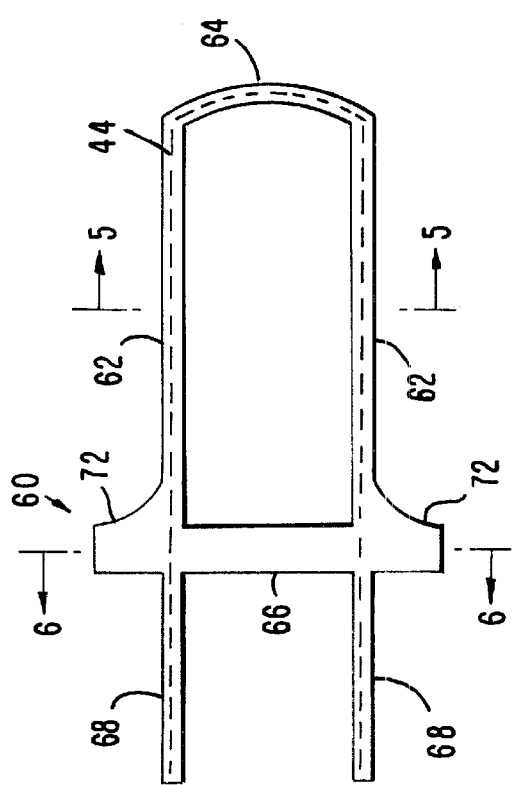

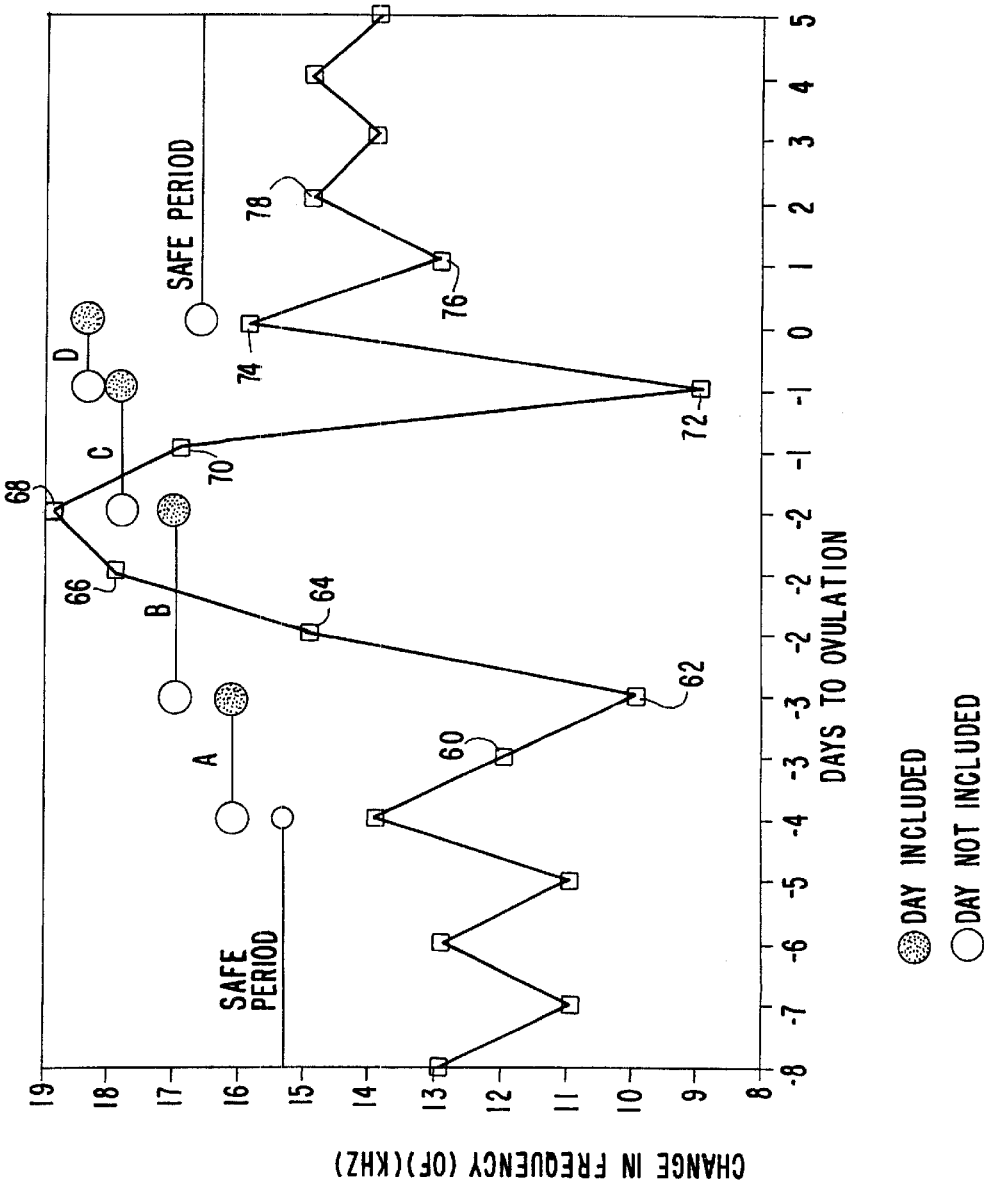

METHOD AND APPARATUS FOR PREDICTING AND DETECTING OVULATION

FIELD OF THE INVENTION

The invention relates to a method and apparatus for monitoring, predicting and detecting ovulation during the menstrual cycle of a human female subject and in mammals generally. More specifically, the invention relates to a method and apparatus for predicting the progress of a female subject's fertility cycle that is based on the measurement and recording of changes in the characteristics and properties of an electrical circuit that result from bringing an oral sensor that forms a part of the circuit into contact with the subject's saliva.

DESCRIPTION OF THE PRIOR ART

The importance of accurately predicting and detecting the onset of ovulation in fertile females has been recognized for many years. Such information is extremely useful as an aid to fertilization, or to prevent fertilization without the need of contraceptive devices or drugs. The art has recognized the need for a device and for a method for monitoring the ovulation cycle in the privacy of the subject's home that is simple to use, reliable, inexpensive and non-invasive.

1. REVIEW OF INFERTILITY PROBLEM IN THE U.S.

The Office of Technology Assessment (OTA), an agency of the Congress of the United States, estimated that from 2–3 million American couples want to have a baby, but either need medical help to have one or will remain unable to have one. While there has been no increase in the overall incidence of infertility in recent years demand for infertility services—mostly conventional medical and surgical rather then in-vitro fertilization (IVF) or other new technology—has steadily increased, with between 300,000 and one million couples annually seeking help. Still, as many as half of the couples seeking treatment for infertility will ultimately be unsuccessful, OTA says.

Americans spent about $1 billion on medical care to combat infertility in 1987, according to the Agency. Less then 1% of all couples seeking infertility treatments try IVF, OTA says; there was some 14,000 attempts at IVF in 1987, involving about $66 million of the $1 billion outlay.

Among infertile couples seeking treatment, 85–90% are treated with conventional medical and surgical therapy. Medical treatment ranges from instructing the couple in the relatively simple methods of pinpointing ovulation to more complex treatments involving ovulation induction with powerful fertility drugs, and artificial insemination (AI). Ovulation induction, surgery, and AI are the most widespread and successful approaches to overcoming infertility.

Two non-coital reproductive technologies—in-vitro fertilization (IVF) and gamete intrafallopian transfer (GIFT)—offer hope to as many as 10–15% of the infertile couples who could not be successfully treated otherwise. These techniques are being practiced with increasing frequency, but proficiency varies widely.

Some 10 to 80 medical teams in the U.S. have established a record of some success with artificial insemination (AI) and invitro fertilization (IVF), and proficiency with GIFT is increasing. However, the remainder of the 169 IVF/GIFT programs in this country have has little or no success to date.

It is apparent that whether the infertility problem is treated with simple or complex treatments, a reliable and accurate method of pinpointing conception is a precisely timed biological event, infertility diagnosis and treatment often involve costs of time away from work, and may involve travel, hospital and hotel costs. The proposed device will reduce the time and costs to infertile couples because it allows couples to pinpoint ovulation at home with a high degree of accuracy and minimal or no medical or professional supervision.

2. REVIEW OF LITERATURE ON OVULATION PREDICTION METHODS

The task of predicting ovulation or the fertile period, therefore, appears to be quite important. One needs only to measure alterations in important to marker molecules in any of a number of biologic fluids that would define the limits of the fertile period or, specifically, ovulation. However, defining these limits involves establishing the life span of both gametes involved in the fertilization process. Estimates of sperm viability in the female reproductive tract range from 2 to 7 days. Unfortunately, good data for such estimates are scarce. In reality, the life span of the ovulated ovum has been suggested to be only as long as 72 hours. However, institutions practicing in-vitro fertilization suggest the mature ova more than 24 hours old (perhaps only 12 hours) are generally incapable of being fertilized and/or producing viable offspring, but their in-vivo life span may be considerably more. Thus, the period of fertility in most women may be from 7 days prior to ovulation to possibly 3 days after. Unfortunately, without more information about functional sperm survival in the female reproductive tract, this interval will continue to be uncertain. Good predictors of this ovulation, therefore, would mark this span of time by being able to coincidently detect changes in more then one hormone or other molecules in biological fluids. Since steroid hormones are produced by the developing graafian follicle and corpus luteum, plasma concentrations of these or their urinary metabolites would be useful markers, and measurements of either plasma or urinary LH or FSH may be helpful, since it is these alone or in combination that lead to follicular and ovum maturation and to ovulation itself. Furthermore, since estrogens and progesterone have a wide variety of biological functions, one might speculate that molecules acutely responsive to their plasma concentration may be useful as fertile period indicators. Also, one would expect that a truly specific indicator of the fertile period and/or ovulation would be a product of the dominant follicle, since it is destined to become the parent of the ovum at ovulation. Changes in electrolyte concentration in various biological fluids (saliva and vaginal mucus) have also been reported as a function of ovulation.

In addition, techniques needed to measure these changes in hormones or hormone- responsive markers must be sensitive, specific, cost-effective, easy to perform as applicable to a clinical or diagnostic setting in which sophisticated equipment is unavailable. The interval of time between samples taken for monitoring also must be considered. The efficacy of predicting the fertile period may increase with a decreasing sample-to-sample interval, and the longest interval allowed to give optimal predictability of a given variable to establish the fertile period must be clearly defined. From known rhythms of alterations in plasma, saliva, and urinary hormones, it appears that the successful monitoring of steroids, peptide, and other factors for the prediction of ovulation would require a daily, or perhaps twice daily, sampling. Under those conditions one could expect to accurately predict the fertile period in at least 90% of normally cycling women. Finally, since no methodology will be successful if it is used incorrectly, it is essential that ovulation prediction techniques be developed that will minimize inconvenience to the user.

3. REVIEW AND COMMENTS ON MOST COMMON FERTILITY METHODS

3.1 The Rhythm Method (Also Known as the Calendar Method or the Ogino-Knaus Method)

Ogino and Knaus showed that regardless of the length of the individual's cycle, the timing of ovulation is relatively constant with respect to the onset of the next menses, but not necessarily with respect to the previous menses. From these studies, both developed formulas to determine a woman's fertile and infertile days on the basis of her own cyclic variations. This marked the beginning of "rhythm" as a valid contraceptive method.

The greatest problem with calendar rhythm is that few women have regular 28-day menstrual cycles. Therefore, timing an event—ovulation—14 days in advance of another event which does not occur with complete regularity is difficult in theory and often impossible in practice. An exact record of at least 6 menstrual cycles, or preferably 12, is necessary even for initial calculations. Thus, for a woman with a menses of 4 days duration, which varied over a 12-month period from intervals of 26 and 31 days, only 12 to 18 cycles would be safe for intercourse including the days of menstruation.

3.2 The Temperature Method

Unlike the calendar method, which depends primarily on the regularity of the menstrual cycle, the thermal or temperature method depends upon identification of a single event—the rise in basal body temperature (BBT). This occurs at the time of ovulation as a result of the elevated progesterone level. The basal body temperature refers to the temperature of the body at complete rest. It varies from person to person and within each individual depending on the time of day, year, the surrounding climatic temperature, and in women, on the phase of the menstrual cycle.

3.3 The Cervical Mucus Method

To practice these methods, a woman must be aware of the sensations of "dryness" and "wetness" in the external parts of the vagina during the different phases and must differentiate between feelings of "stickiness" and of "lubrication." If she wants confirmation of her sensations she can wipe her vagina with a tissue before urination and examine the physical properties of the mucus, but she is advised not to depend solely on tactile examination of the vagina.

A more quantitative cervical mucus conductivity device has recently been promoted as providing a method of estimating the fertile period. The operation of the device, known as the Cue Fertility Monitor, is based on the hypothesis of changing estradiol and/or progesterment. As estrogen levels rise in the pre-ovulatory period, mucus conductivity rises, and then falls with increasing progesterone concentration. The Cue method uses both vaginal and salivary electrical resistance to predict not only ovulation, but also the pre-ovulatory period for up to one week prior to ovulation. The premise is that peek salivary ion concentration occurs 6–7 days prior to ovulation and then declines throughout the remainder of the menstrual cycle. Vaginal ion concentrations apparently reach their nadir approximately one day before ovulation and then rise significantly. As will be described in more detail below, the Cue Fertility Monitor has been promoted as giving advance notice of ovulation, but it requires vaginal measurements in addition to the saliva measurements to confirm the time of ovulation.

4. REVIEW AND COMMENTS MOST COMMON BIRTH CONTROL METHODS

4.1 Barrier Methods

4.1.1 The Condom

Effectiveness: The condom has a failure rate of about 2% when used as directed. Typically, it has a failure rate of about 12%. For close to 100% protection, the condom should be combined with spermicidal foam, cream or jelly.

Cost: The price for latex condoms may range from $3 to $18 for a dozen. Skin condoms may range from $2 or more each. Other brands may cost more.

Heath Affects: Condoms may produce an allergic reaction.

4.1.2 The Diaphragm

Effectiveness: The typical failure rate is about 18%. Effectiveness can be enhanced if the women's partner also uses a condom.

Cost: The cost of the diaphragm may range from $12 to $25. The medical examination and the fitting of the diaphragm can cost from $50 to $100. Spermicidal jellies and creams that are used with the diaphragm begin at about $8.

Health Effects: Some women have a slightly increased risk of repeated urinary tract infections, which may be caused by the pressure of the rim on the urethra or spermicide. Diaphragms can also be vaginal trauma. It causes a disruption of the vaginal epithelium, which leads to lesions on the vaginal walls, which can serve as places for the proliferation of microorganisms.

4.1.3 The Cervical Cap

Effectiveness: The failure rate ranges from 8% to 19%. To increase effectiveness the woman's partner may also use a condom.

Cost: The cervical capo ranges from $30 to $40. The medical examination involving a preliminary pelvic examination, PAP test and fitting can range from $30 to $100.

Health Effects: There is a theoretical risk of toxic shock syndrome if the cap is worn more then 72 hours. The regular use of the cervical cap can lead to the vulnerability of the epithelium, the cell layer that lines the cervix, to the human papoilloma virus. This may then lead to cervical cancer. There is also a risk that the cap may irritate the cervix.

4.1.4 Contraceptive Sponge

Effectiveness: The typical failure rate is about 18%. This rate increases for women who have previously given birth.

Cost: The cost is approximately $1.50 per sponge. They are usually sold in packages of 3, 6, or 12.

Health effects: there is a small chance of toxic shock syndrome. The sponge may tear if worn more than 48 hours. Allergic reaction may also occur. Since the sponge absorbs vaginal fluid during the intercourse, it may lead to vaginal dryness.

4.1.5 Spermicide

Effectiveness: They have a first year failure rate of about 21% to 22%.

Cost: Creams and jellies range from $7 to $13. Foams cost between $9 and $11 per can.

Health Effects: They may cause irritation or allergic reactions

4.2 Hormonal Methods

4.2.1 The Pill: Combined Oral Contraception

Effectiveness: It should be taken every day at approximately the same time. A Pill that includes synthetic estrogen is extremely effective. A Pill that contains at least 30 mcg of estrogen has about 1% to 2% failure rate. Pills that contain 20 mcg of estrogen have failure rate of 2%. The effectiveness of oral contraceptives can be lessened by a number of commonly prescribed drugs.

Cost: Physical examination range from $50 to $150 plus charges for the necessary laboratory test. The cost of refilling a birth control prescription may range from $12 to $30 for a month's supply.

Health Effects: The use of oral contraceptives can lead to the development of cardiovascular complications. It may also lead to an increased risk of cervical dysphasia (abnormal cell changes) and cervical cancer.

Pills can also cause cervical erosion, which will lead to chlamydeous cervicitis. The pill may accelerate gallbladder problems for women who are prone to this disorder. The pill has been associated with an increase in the incidence of rare liver tumors and liver cancer.

The pill has side effects such as nausea, Vaginitis, Urinary Tract Infection, changes in menstrual flow, breakthrough bleeding, breast-feeding problems, headaches, diabetes, breast swelling, fluid retention, weight gain, depression, and skin problems, gum inflammation, and virus infections.

4.2.2. The Pill: Progestin-Only Mini-Pills

Effectiveness: The failure rate is about 2% to 3%. This rate decreases with age.

Cost: Physical examination can range from $50 to 150 not including the charges for laboratory test. Progestin-only pills cost about $25 to $45 for a month's supply.

Health effects: Functional Ovarian cysts may develop. There is a greater risk of Entopic Pregnancy if pregnancy occurs during the use of the mini-pill. The most common side effect of the mini-pill is menstrual disturbances. The effects seen with the combination pill also occur but are less common with the Progestin-only pill: headaches, weight gain, cervical erosion, jaundice allergic reaction, depression, gastrointestinal disturbances, and breast changes.

4.2.3. Norplant

Effectiveness: The pregnancy rate is 0.2% in the first year of use, 0.5% for the second year, 1.2% for the third year, and 1.6% for the fourth year. The overall effectiveness rate for the entire five years is 96%. Women who weigh over 154 pounds have an increased risk (5.1%) of pregnancy beginning in the third year of use.

Cost: Norplant implants cost $350. There is also a cost for insertion ($150 to $200) and removal ($70 to $150); If Norplant is used for all five years, the cost averages to about $100 per year.

Health effects: There are side effects such as irregular menstrual bleeding, cholesterol changes, headaches, functional ovarian cysts, weight changes, infection at the site after insertion, expulsion of one or more capsules from under the skin, and mood changes. Some uncommon side effects include acne, unwanted hair growth, nervousness, nausea, dizziness, changes in appetite, and hair loss.

4.3 The Intrauterine Method

4.3.1. Intrauterine Devices (IUDS)

Effectiveness: The typical failure rate is 3%. This percentage is lower among women over thirty. The two types of IUDs are Progestasert and ParaGard. The Progestasert has a failure rate of about 2%. The ParaGard has a failure rate of less than 1%.

Cost: Costs range from about $100 to $600. This includes the IUD itself, counseling, a physical exam, blood tests, and insertion.

Health Effects: There is a risk of Pelvic Inflammatory Disease. Pregnancy can occur, and if it does there is a risk of an n entopic pregnancy. Peroration can occur unb which the IUD can perforate the uterus (or cervix). It maybe expelled. It may become embedded in the lining of the uterus. It may cause side effects such as bleeding, cramping, and pain.

4.4. Surgical Methods

4.4.1. Female Sterilization: Tubal Occlusion

Effectiveness it is more than 99% effective.

Cost: The cost of a tubal occlusion can range from $700 to $3,000.

Health Effects: Major complications are infrequent. Complications can result from the surgery itself, such as infection, internal bleeding, or damage to organs and tissues. The most common long-tern complication of tubal sterilization is an entopic pregnancy.

4.4.2. Male Sterilization: Vasectomy

Effectiveness: There is a failure rate of 0.5% to 1%.

Cost: A vasectomy costs between $300 and $1,000.

Health Effects: Complications are rare. The most common complication is a hematoma, which is a mass of clotted blood. An infection may develop (1.5% to 3.4%) near the site of the incision. Epididymitis occurs in 0.3% of cases.

5. PREDICTIVE METHODS BASED ON BIOCHEMICAL PARAMETERS

From the above summary description, it will be apparent that substantial research efforts and expenditures have been made and are continuing to be made in connection with the effects of infertility, fertility and population control. Many of the problems associated with these issues could be resolved if there existed a reliable means of determining or predicting in advance when ovulation was going to occur.

In view of the above, various methods have been disclosed in the literature for predicting ovulation or the progress or stage of the subject's fertility cycle that are based on measuring changes in, or the values of any of a number of biological fluids that define the limits of the fertile period or, specifically, ovulation. However, defining these limits involves establishing the life span of both gametes involved in the fertilization process. Estimates of sperm viability in the female reproductive tract range from 2 to 7 days. Unfortunately, good data for such estimates are scarce. In reality, the life span of the ovulated ovum has been suggested to be only as long as 72 hours. However, institutions practicing in-vitro fertilization suggest that mature ova more than 24 hours old (and perhaps only 12 hours) are generally incapable of being fertilized and/or producing viable offspring. Other authorities suggest that their in-vivo life span may be considerably longer. Thus, the period of fertility in most women may be from 7 days prior to ovulation to possibly 3 days after. Unfortunately, without more information about functional sperm survival in the female reproductive tract, this interval will continue to be uncertain. Good predictors of ovulation, therefore, mark this span of time by being able to coincidentally detect changes in more then one hormone or in other molecules in biological fluids. Since steroid hormones are produced by the developing graafian follicle and corpus luteum, plasma concentrations of these or their urinary metabolites can be useful markers, and measurements of either plasma or urinary LH or FSH may be helpful, since it is these alone, or in combination, that lead to follicular and ovum maturation and to ovulation itself. Furthermore, since estrogens and progesterone have a wide variety of biological functions, it has been suggested that molecules acutely responsive to their plasma concentration may be useful as fertile period indicators. Also, it would be expected that a truly specific indicator of the fertile period and/or ovulation would be a product of the dominant follicle, since it is destined to become the parent of the ovum at ovulation. Changes in electrolyte concentration in various biological fluids, including specifically saliva and vaginal mucus, have also been reported as functionally related to the onset of ovulation.

In addition, techniques needed to measure these changes in hormones or hormone- responsive markers must be sensitive, specific, cost-effective, easy to perform as applicable to a clinical or diagnostic setting in which sophisticated equipment is unavailable. The interval of time between samples taken for monitoring must also be considered. The efficacy of predicting the fertile period should increase with a decreasing sample-to-sample interval, once the longest interval allowed to give optimal predictability of a given variable to establish the fertile period is defined. From known rhythms of alterations in plasma, saliva and urinary hormones, it appears that the successful monitoring of steroids, peptide, and other factors for the prediction of ovulation requires a daily, or even twice daily, sampling. Under optimum conditions one could expect to accurately predict the fertile period in at least 90% of the subjects having a normal fertility cycle. Finally, since no methodology can be successful if it is used incorrectly or inconsistently, it is essential that the ovulation prediction method and apparatus be of minimum inconvenience to the subject and that it require minimal manipulation by the subject.

Various methods of predicting ovulation based on biochemical changes in body fluids, such as vaginal mucus, urine or saliva, have been proposed. For example, U.S. Pat. No. 3,434,801 discloses a test for chloride ion concentration that is indicative of sodium chloride concentration; U.S. Pat. No. 4,385,125 proposes a method of detecting ovulation by monitoring dodecanol concentrations in saliva; U.S. Pat. No. 5,914,271 discloses monitoring calcium and magnesium concentrations in saliva as an ovulation predictor; and U.S. Pat. No. 5,109,865 discloses a device for measuring sodium ion concentration in vaginal mucosa to determine pregnancy. It is also known from the literature that the concentration of sodium and potassium-containing compounds in the human female's saliva vary with her menstrual cycle. During ovulation, the concentration of sodium and potassium ions reaches a maximum. Measuring the variation in concentration can give a precise indication of the fertile period and the ovulation time. However, as disclosed in U.S. Pat. No. 4,770,186, the method of measuring the concentration of specific ions is expensive and not readily accomplished in a portable, hand-held device that must be used on a daily basis.

The above-described and other methods and apparatus for predicting the advance of a female subject's fertility cycle are based on direct measurement of one or more compounds in the subject's saliva or other bodily fluid. These methods are direct, i.e., the saliva is analyzed directly for the presence of a particular chemical compound or biological material. An alternative method is by indirect measurement, as by measuring another property that is affected by the composition of the saliva. One such indirect method is disclosed in U.S. Pat. No. 4,770,186 ("the 186 patent") and employs the subject's saliva to complete the circuit between a plurality of conducting elements in a probe that is placed in the subject's mouth. The disclosure of U.S. Pat. No. 4,770,186 is incorporated herein by reference. Using appropriate circuitry, the relative resistivity as measured by the same probe is recorded on a daily basis and a plot of the so-called "saliva electrical resistivity", or "SER", is prepared. As reported in this disclosure, the value of the resistivity increases and decreases in a predictable pattern in relation to the days before and days following ovulation. Again, according to the disclosure, the pattern is sufficiently consistent from one period of ovulation to another to permit the subject to make a visual determination, or at least an estimation of when ovulation will occur based upon the data points plotted. The numerical values of the SER observed by the subject are graphically plotted on the vertical or Y-axis and the days before and days after the day of ovulation are plotted on the horizontal or X-axis.

According to the disclosure of the '186 patent, the absolute values of the SER will vary among subjects who are at precisely the same stage in their respective cycles and it is therefore necessary to look at the graphical plots or relative values of the historical SER data to predict the subject's fertile period. When the SER values are plotted against the days to ovulation, it is stated that a generally consistent pattern is observable from one cycle to another, and that each cycle can be divided into a series recognizable stages or zones. However, the method described in the '186 patent also requires the accumulation and recording of similar daily electrical resistance data for the subject's vaginal fluids in order to provide an accurate and reliable prediction of the fertile period. It has also been determined that the measured values of the SER are subject to variations caused by factors other than the stage of the subject's menstrual cycle. The variations can be caused by changes in the subject's general health, stress, and the like. As will be understood by one of ordinary skill in the art, such variations will have an adverse effect on the pattern or plot of the SER values with the result that the data becomes unreliable as a basis for predicting the fertile period.

It has also been found, contrary to the specific teachings of the '186 patent, that the plotting of electrical resistivity of the vaginal mucus is a much more reliable and accurate indicator of the ovulation cycle than the SER method. In this regard, it is now known that the differences in electrical resistivity of the vaginal mucus are greater and produce a more significant change during the critical periods of the subject's fertility cycle than is suggested by the disclosure of the '186 patent.

A device for making and recording quantitative cervical mucus conductivity measurements has been promoted for predicting the fertile period. The device, offered commercially as the Cue Fertility Monitor, measures both vaginal and salivary electrical resistance to predict not only ovulation, but also the preovulatory period for up to one week prior to ovulation. The cost of this device is relatively expensive and questions regarding its reliability, ease of use and the subject's ability to interpret the readings have been raised. Although the Cue Fertility Monitor has been promoted as giving advance notice of ovulation based on use only of an oral probe in contact with the saliva, reports suggest that measuring salivary electrical resistance alone using the Cue device is not reliable and that vaginal measurements are required to accurately predict the time of ovulation. However, as suggested in the literature of the prior art, it is much more desirable to employ a method and apparatus in which the subject can use an oral sensor or probe to contact her saliva, than it is to rely upon a method and apparatus that requires contact with the vaginal mucous.

It is, therefore, a principal object of the present invention to provide a method and apparatus for reliably and consistently predicting and detecting ovulation in which the subject's saliva is employed to indirectly provide data related to the progress of the subject's fertility cycle and to the subject's stage in the fertility cycle.

Another object of the invention is to provide an improved method and apparatus for determining the stage of the subject's fertility cycle that is based on a parameter whose changes during the cycle are substantially linear.

It is a further object of the invention to provide a method and associated apparatus that is based on the measurement of a characteristic of the saliva on at least a daily basis, and the visual display of data or other indicia derived from such measurements that will provide an accurate prediction of the subject's fertility cycle and the contemporaneous stage of the cycle.

It is also an object of the invention to provide a device by which the subject utilizes a non-invasive, single-use disposable sublingual, lingual or bucal probe to obtain at least a daily measurement of a characteristic of the saliva and the device provides a visual display from which the subject can determine with reliability the stage of her fertility cycle.

An additional object of this invention is to provide a user-friendly, self-interpretive device and method to predict and confirm ovulation and the fertility cycle.

Another object of the invention is to provide a reliable, inexpensive disposable oral sensor for use in the method and apparatus.

A further object is to provide a subject with an historical record of monitoring data that will be of use in the proper treatment of subjects with fertility problems and to permit them to monitor the progress of any treatment and any improvement in her condition.

Another object of the invention is to provide a hand-held, portable, battery-powered device that does not impose any environmental or personal restrictions on the time, place or manner of its use.

A still further object is to provide an inexpensive, simple and accurate method and apparatus for monitoring and predicting ovulation, that is a useful means for birth control.

SUMMARY OF THE INVENTION

The above objectives, as well as other benefits and advantages, are achieved by the present invention which provides a method and apparatus for predicting and identifying the fertile period of human female subjects and other female mammals. In a preferred embodiment, the invention provides a direct visual display of the interpretations of one or more daily measurements utilizing a disposable oral sensor in combination with an electrical circuit, a programmed microprocessor, memory and display device.

In its most elemental form, the invention utilizes an oral sensor that, together with novel electrical circuit, measures the change in frequency in the circuit due to the contact of the oral sensor with an electrolyte in a liquid medium, i.e., the subject's saliva. The amount and direction of the change in frequency varies with the concentration of electrolytes in the medium. An indicator displays the change in frequency, or in a preferred embodiment of the apparatus, analyzes the change in frequency and display its results.

A method of indirectly monitoring changes in concentration levels of electrolytes on a medium is provided. An oral sensor whose apparent capacitance varies with the concentration level of the electrolytes is provided. A means of relating the changes in electrolytes concentration by detecting changes in the oral sensor's effect on an oscillator circuit is also provided.

An oral sensor for use in monitoring concentration levels of electrolytes is also provided. A capacitor-like element, the oral sensor's characteristics vary with the concentration of electrolytes. The oral sensor is used with devices that detect changes in the oral sensor due to the concentration level. One preferred type of detection device uses an oscillating circuit of which the oral sensor is a component.

The method and apparatus operate on the principle of indirect measurements of the properties of the subject's saliva which vary in a predictable pattern during the fertility cycle. Significantly, the indirect measurements of the characteristic of the electrical circuit are found to produce a more nearly linear plot than other methods and techniques described by the prior art. Most importantly, the combination of the oral sensor design and the electrical characteristic chosen for measurement produce a synergistic result, so that the reliability of the data and associated tabulations are not affected by factors such as the subject's illness, an injury, physical or mental stress, diet, and the like.

The oral sensor of the invention is so constructed that it most nearly resembles a capacitor, and will be referred to herein as a "capacitive oral sensor" or, for convenience, simply as an "oral sensor". As used herein, "capacitive oral sensor" means a component for use in an electrical circuit and that is of an appropriate size and shape to be placed in the subject's mouth to be intimately contacted and preferably coated, at least in part, by the subject's saliva. The oral sensor of the invention is formed from a pair of exterior layers of conductive material that are electrically isolated or insulated from each other. Positioned between the first and second exterior layers is a third interior layer of conductive material that is electrically isolated from one of the exterior conductive layers by a layer of non-conductive material and spaced from the other exterior conductive layer by a perforated non-conducting layer of material so that the surface of the third interior layer of conducting material is in contact with one of the exterior layers in the region of the perforations. The third interior layer of conducting material is also perforated so that the two opposing layers of non-conducting material are in contact with each other in the region of the perforations. When the capacitive oral sensor of the invention is incorporated in an oscillator circuit and placed in contact with an electrically conductive solution, or electrolyte, containing sodium ions, e.g., aqueous sodium chloride, it produces a substantially linear change in frequency, df, in the circuit.

The capacitive oral sensor constitutes a part or component in an oscillator circuit that operates at one design frequency when a fresh oral sensor is installed and at a different frequency when the oral sensor is brought into contact with the subject's saliva. The invention comprehends a method that is based on measuring and recording frequency changes based on daily readings to first establish a baseline of data for her menstrual cycle, that in one embodiment, can be displayed graphically; and subsequently, to compare daily frequency changes, or differences in frequency, df, with the baseline data to predict and display the subject's current status relative to her menstrual cycle.

The invention is preferably housed in an appropriately configured hand-held device, is battery-powered and is portable so that it can easily be transported in a purse or luggage when the subject is traveling. The apparatus also includes an appropriately programmed microprocessor/controller, memory, display means and frequency-measurement means provided for the purpose, along with novel algorithms to process the measurements and which can predict ovulation 5–8 days in advance. The apparatus and method accurately measure and analyze salivary properties utilizing only an oral sensor, algorithms and a microprocessor/controller. The invention obviates the need for invasive vaginal measurements and the attendant fear of vaginal infection.

The recruitment of dominant follicle in the female's ovaries causes significant changes in bodily fluid electrolytes. The capacitive oral sensor of the invention indirectly measures the changes in bodily fluid electrolytes in the saliva by use of an oscillator circuit and a related processor and algorithms adapted to measure frequency values and differences, record the data and compare it to historical baseline and other historical data. This indirect measurement is made in terms of the frequency change in an oscillator circuit that is designed for use in conjunction with the oral sensor. When compared to a baseline of data obtained for the subject, the measurement of these changes are utilized to predict ovulation five to eight days in advance. A reliable and accurate ovulation prediction device can be used by couples trying to conceive or, conversely, to avoid pregnancy, i.e., for contraception.

The method of the invention uses the measured variation in frequency due to changes in the permeability of the non-conducting dielectric material used in the capacitive oral sensor. As presently understood, when the concentration of sodium ion and other electrolyte changes with the biological change of the female, the frequency of the oscillator circuit will change when the oral sensor is wetted with the subject's saliva.

In a preferred embodiment, the apparatus includes a housing with a display panel located on the top front or face. An on/off switch is located toward or on the right side wall for easy access by the subject. The oral sensor socket is located in or adjacent the top wall of the unit. The oral sensor is provided with electrical conducting leads adapted to be received in the oral sensor socket. A start button or switch can also be located on the front or sidewall. It is conveniently located to be used by the thumb of the same hand. It is pushed instantaneously after the oral sensor is in the mouth. Power for the device is preferably supplied by a 7.2 VDC (9 VDC nominal) battery that should last for about 6 months with an average of three minutes of daily use.

The device is equipped with non-volatile memory that can store up to three years of daily measurements. The accumulated data can be downloaded to a personal computer via an internal connector and appropriate software in response to a switch or coded signal transmitted to the microprocessor for this purpose.

The change in frequency (df) is monitored daily and a new or fresh oral sensor is installed in the circuit before each daily measurement. The daily frequency measurement data is recorded in the memory of associated data storage means and is processed and compared with other historical data, i.e., the data taken on previous days, and the change in frequency recorded, compared with the historical or baseline df and an appropriate signal generated and transmitted to the display means. As will be described in more detail below, the significance of having successive frequency change measurements going up or down signifies the beginning of each successive stage of the fertility cycle before or after the time of ovulation.

If a preferred embodiment, a limited access reset button is provided so that when the unit is used by another subject, the device can be reset to start accumulating data for the new subject. All the old data of the previous subject can either be erased or transferred to another data storage register associated with the first subject's personal identifying indicia.

The method and apparatus of the invention can be used with mammals other than humans. The menstrual cycles of most mammal species that have been kept for food, breeding as pets, zoological specimens and the like, have been documented. Data can be gathered on a daily or other regular basis that is relevant to the fertility cycle of the mammal and the purpose, e.g., for natural or artificial insemination when the female animal is in the fertile stage. The size and configuration of the oral sensor can be adapted for use with different types of animal. For example, the oral sensor support structure can be made larger and able to withstand biting or chewing by the subject. Instead of being inserted directly into a housing that also contains the circuitry, power supply and display means, the oral sensor can be incorporated into a hand-held probe that is connected by a shielded cable to a remote device; or the probe can include a portable power supply, e.g., a battery and digital memory means for recording the frequency data, which is later downloaded for processing in a remote device.

The invention thus provides a method of birth control by indirectly monitoring concentration levels of electrolytes in saliva with an oral sensor that changes the frequency of an associated oscillator circuit when in contact with the saliva. Interpreting the change in frequency indicates the onset of ovulation.

BRIEF DESCRIPTION OF THE DRAWINGS

The invention will be described in further detail below and with reference to the drawings in which:

FIG. 3 is an exploded perspective view of one preferred embodiment of a capactive oral sensor of the present invention;

FIG. 4 is a top plan view of one embodiment of a supporting frame for the oral sensor of FIG. 3;

FIG. 5 is a cross-sectional view of the frame of FIG. 4 taken along section line 5—5;

FIG. 6 is a cross-sectional view of the frame of FIG. 4 taken along section line 6—6;

FIG. 7 is a graphic representation illustrating the pattern of the change in frequency vs. time for a subject during her fertility cycle;

DETAILED DESCRIPTION OF THE INVENTION

Figure 1:
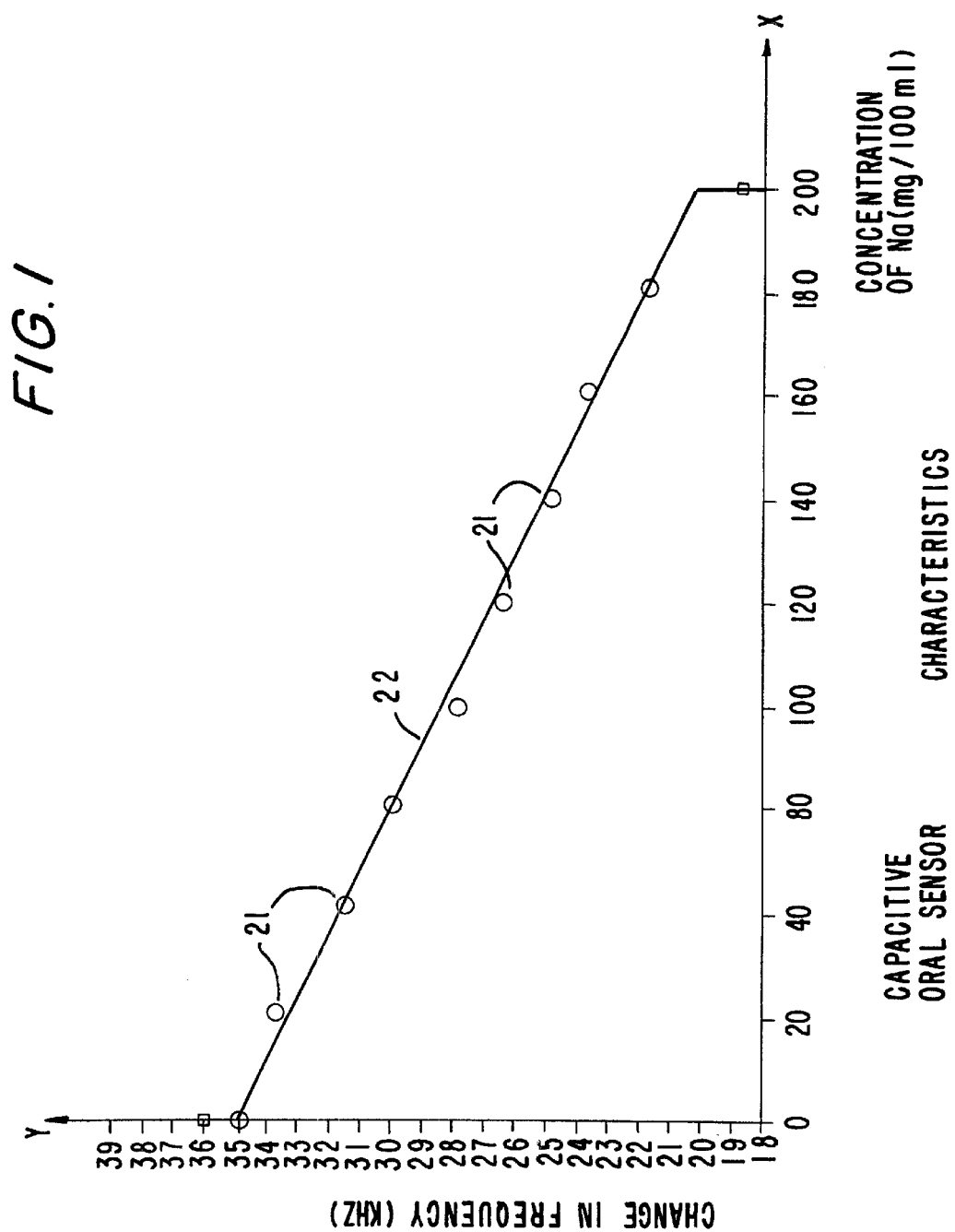
FIG. 1 is a graphic representation illustrating the functional relationship between the change in frequency response of an oral sensor and the concentration of an electrolyte solution representative of that found in saliva.

Referring to FIG. 1, there is illustrated a graphic representation of the relationship between changes in concentration of sodium ions in the form of sodium chloride in an aqueous solution versus the relative frequency changes experienced in an oscillator circuit when the capacitive oral sensor of the invention is placed in contact with the salt solution. As noted, the X-axis represents the salt concentration in mg/100 ml of aqueous solution and the Y-axis is the frequency of the circuit measured in KHz. As can be seen from a plot of the individual frequency readings 21 at the indicated concentration levels, utilizing the oral sensor and method of the invention, the relationship between frequency and concentration is essentially linear. As previously noted, the concentration of electrolytes in the female subject's saliva vary in accordance with a pattern that can be determined and plotted for each individual subject to provide a baseline. The baseline data is then utilized in the method and apparatus of the invention to determine the subject's stage in her fertility and at appropriate times, predict the days to ovulation during subsequent menstrual cycles. The linear relationship obtained utilizing the oral sensor in the apparatus and method of the invention provides a significant advantage over the prior art devices and methods.

Figure 2:
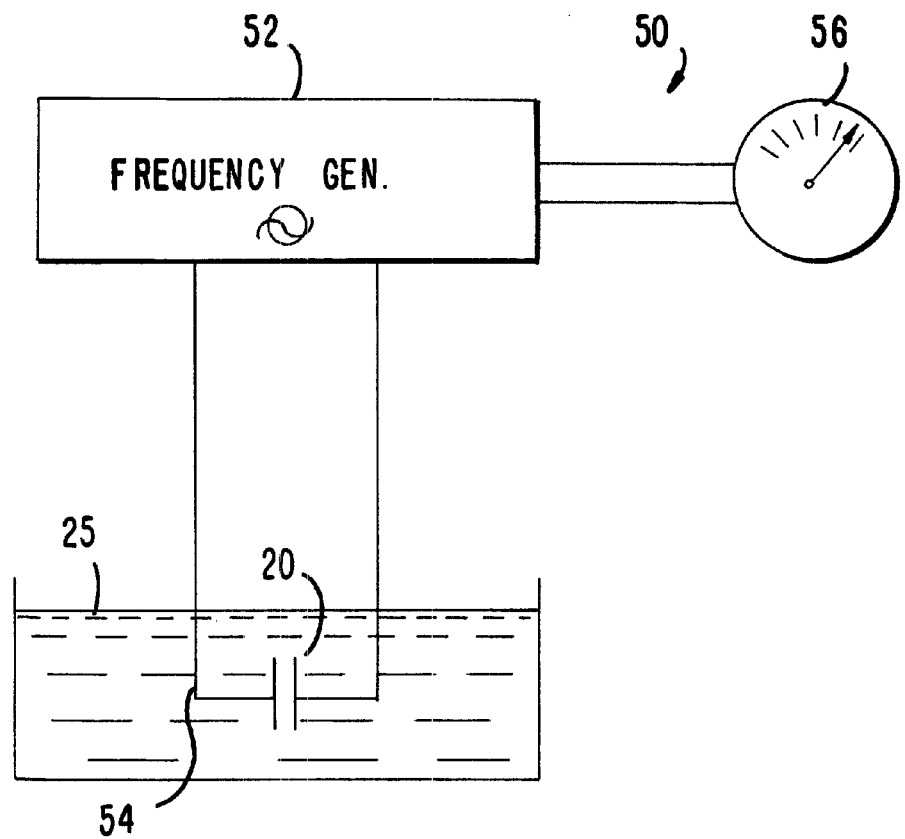
FIG. 2 is a simplified schematic illustration of an electrical circuit and capacitive oral sensor in contact with an electrolyte solution.

Referring now to FIG. 2, there is schematically illustrated in simplified form the arrangement for obtaining the data of FIG. 1. The oscillator circuit, generally referred to as 50, includes an oscillator 52 which is capable of generating a precise frequency, and frequency measuring means 56 for measuring the frequency of the circuit. Oral sensor 20 is electrically linked to the frequency generator by conductors 54. In order to obtain the datapoints 21 of FIG. 1, oral sensor 20 is immersed in electrolyte solution 25 having a known concentration of ions, in this case, sodium ions. In order to obtain additional datapoints, a fresh oral sensor 20 is utilized in circuit 50 and placed in contact with an electrolyte solution of a different concentration. The frequency response of the circuit 50 is dependent upon the characteristics of the sensor 20. When the sensor contacts saliva or other electrolyte containing solution 54, the characteristics of the sensor change, causing a change in the frequency response of the frequency generator circuit 50. The magnitude of the change in frequency due to the contact with the solution 54 is believed dependant upon the concentration of electrolytes. The frequency due to sensor contact with the solution is determined from the frequency meter 56. Comparing this frequency with a baseline frequency, such as the frequency of the circuit without electrolyte contact, allows the change in frequency (df) to be calculated. It will be understood that the method and apparatus described in connection with FIGS. 1 and 2 is analogous to that employed with the female subject where a fresh oral sensor is placed in contact with the subject's saliva to obtain daily frequency readings.

The construction of a preferred embodiment of the capacitive oral sensor of the invention will be described with reference to the exploded view of FIG. 3 and to FIGS. 4, 5 and 6. Referring now to the exploded view of FIG. 3, oral sensor 20 comprises a plurality of strips of an electricaly conductive material and an insulating material laminated together to form a single unit. The conductor is preferably aluminum; the nonconductor (NC) or dielectric material can be a polyethylene terephthalate (PET) material. A continuous layer of aluminum 30 adjoins a layer of dielectric 32, which in turn adjoins a second layer of aluminum 34, which in turn adjoins a second continuous layer of dielectric 36, which in turn adjoins a continuous end layer of aluminum 38. Aluminum layers 30 and 34 are electrically connected and contact each other at contact points 41 corresponding to the perforations 40 in dielectric layer 32. The aluminum layer 38 is not electrically connected to the other aluminum layers 30, 34, but is separated from them by the dielectric layer 38. The multiple layers of conductive aluminum and dielectric material when laminated together allow additional material to be added to the sensor in a compact form for obtaining the desired df characteristics. Aluminum layers 38 forms one side 48 of sensor 20, layer 30 forming the other side. The distal ends 51 and 53 of metal layers 30 and 38, respectively, form the electrical contacts that engage a socket (not shown) which forms a part of the oscillator circuit in which the oral sensor is an operative elements.

Each respective aluminum and dielectric strip 30, 32, 34, 36, 38 is approximately 0.02 mm in thickness. The oral sensor is formed by combining the individual layers together under heat and pressure in a heat transfer process as is known in the art. Connectors 40 and 42 are formed by providing perforations or cutouts in the respective layers of aluminum and dielectric through which the connectors are formed during the heat and pressure process to form the sensor.

The perforations are approximately 2.5 mm in diameter and four are provided in each of strips 34 and 36. The open area formed by the perforations constitute about five per cent of the total area of each strip. The oral sensor is approximately 5 cm in length and approximately 0.7 cm in width, which is preferable to the apparatus further described herein. The aluminum is preferable at least 99.9% pure and the dielectric is preferable homogeneous PET material of the best commercial grade.

With reference to FIG. 4, a sensor supporting frame 60 is provided to receive oral sensor 20 in a flat, edge-supporting relation to insure the integrity of the sensor when it is placed in the subject's mouth and also to provide means for inserting, securing and removing the sensor leads from the device which houses the oscillator circuit, as will be described in more detail below. The frame 60 includes parallel side supports 62 joined at their distal ends by end support 64 and by hollow cross member 66. A pair of projecting legs 68 aligned longitudinally with sidewalls 62 complete the proximal end of frame 60. As shown in the cross-sectional view of FIG. 5, side supports 62 and end support 64 are provided with a channel or groove for receiving the edges and distal end of laminated sensor 20 in a close-fitting and supporting relation. Hollow cross member 66 is provided with a corresponding longitudinal opening to receive in passing relation the body of sensor 20. Legs 68 are also provided with grooves 70 to support and retain sensor 20 along its edges at the proximal end. In a preferred embodiment, frame 60 is manufactured from PET and the sensor is secured in the frame after assembly by heat and pressure. Laterally extending arms 72 are provided to facilitate the handling of the sensor assembly and its installation and removal from the contact socket forming part of the oscillator circuit that is contained in the housing of the device. As described above, contacts 51 and 53 define the distal end of oral sensor 20 and extend between legs 68 of frame 60. It will aslo be understood taht oral sensor 20 can be provided with other types of contacts for threaded and bayonet socket engagement.

In a preferred embodiment of the invention, each oral sensor is hermetically sealed in a transparent sterilizable wrapper and the sealed package is sterilized. Each package is provided with a release means extending around its periphery to facilitate the opening of the package and removal of the portion covering the distal end of the sensor where the contacts are located. It is also preferred that the proximal end of the oral sensor that is to be placed in the subject's mouth be kept clean and free of contact with the subject's fingers or any contaminants that could affect the accuracy of the frequency measurement to be taken. The wrapper and other instructions for use of the device instruct the subject to hold the package in one hand and to remove only the distal end of the wrapper and insert the sensor contacts into engagement in the housing using the proximal end of the wrapper to guide and secure the sensor into the socket.

When utilizing the oral sensors constructed in accordance with the above description, such variations as might be expected to occur in a manufacturing process have not been found to affect the accuracy of the data obtained and its application in the method of the invention. The establishment of quality control standards and the routine testing of each sensor or of random samples in accordance with well established principles will ensure the reliability of the method. A further safeguard is provided by including as an additional step in the method of the invention, the measurement of the frequency of the circuit when a new oral sensor is inserted into the device and the comparison of that frequency to determine that it is within a determined range. If the fresh oral sensor provides a frequency outside of the acceptable range and appropriate signal is generated, e.g., audible or visual, to alert the subject and also to prevent any data generated by subsequent contact of the oral sensor with saliva from being used in the method.

It will also be understood by those of ordinary skill in the art that some variation in frequency characteristics of the oral sensor that result from manufacturing processes can be accounted for by performing the additional step(s) of measuring the frequency of each new oral sensor when it is inserted in the device, recording that frequency measurement, measuring and recording the frequency when the oral sensor is contacted with the subject's saliva, calculating the difference in the two frequency measurements and comparing the difference to the historic data. Alternatively, the frequency of the circuit can be measured when a fresh oral sensor is placed in the device, the frequency value compared to the predetermined acceptable value, or range of values, and an appropriate change made to the circuit, e.g., by adjusting the frequency of the operation of the oscillator.

In the practice of the method of the invention, as an ovulation predictor, the optimum results are obtained when the df readings of the subject's saliva are measured routinely, preferably on a daily basis. In a preferred practice of the method of the invention, the subject begins taking daily readings the first day after bleeding during a menstrual cycle ends. Measurements utilizing a fresh oral sensor are preferably taken at approximately the same time each day, preferably immediately after awakening and prior to any activity such as washing, tooth brushing, breakfast, smoking or other physical activities. To obtain the measurement, the sensor 20 is placed under the tongue in contact with the saliva. The oscillator circuit of which the oral sensor is a component is turned on and the df of the oscillator circuit containing the sensor is observed or determined by appropriate solid state measuring means and recorded. The readings can be plotted as illustrated in FIG. 7 to provide an overview of the subject's historical baseline data or any subsequent cycle, or portion of a cycle. Such graphic plots can be prepared by downloading the data from the handheld device for processing by an appropriately programmed general purpose computer, or PC, and displayed electronically on a monitor or printed. In the illustrative example of FIG. 7, the df readings are shown on the Y-axis, the day(s) to ovulation on the X-axis.

Utilizing the oral sensor of the invension, the functional relationship between df and concentration for the oral sensor used is linear, the data displayed in diagram of FIG. 7 represents the relative changes in concentration levels of electrolytes in the subject's saliva. Thus, the df readings can be used to predict the onset of ovulation by analyzing changes in concentration based on the diagnostic theories and models previously developed in the field.

A preferred method of analyzing the data will be described with continuing reference to FIG. 7. The Y-axis is df, the X-axis representing the days to ovulation as determined by analysis of this particular data. Each successive day on the X-axis represents a reading taken the next day, even though it may be assigned the same number representing the days to ovulation as an adjacent reading. This method of recording and displaying the data is utilized due to variations that can occur in a subject's menstrual cycle and will be further discussed below. As will be recognized, the analysis of such readings can be done manually or by an electrical process utilizing an appropriately programmed processor to carry out the analysis and display the results.

In the diagnostic analysis illustrated in FIG. 7, the subject is considered to be in a "safe period" when not in any of the ovulation stages A, B, C or D. By definition, there is a low probability of ovulation in the "safe" stage. While the subject is in the "safe period," two successive readings 60, 62 showing a continued decrease in df is indicative of symptoms that the subject has entered Stage A whereby ovulation is likely to occur in three days. If an automatic device is used in accordance with a preferred embodiment of the invention, the device will display a message indicating three days to ovulation. Since it cannot be determined that Stage A has been reached until the second successive decrease in df, 62, an automated device will indicate stage A beginning at reading 62. Reading 60, when taken, will lead to an indication of "safe period".

Once Stage A is indicated after the second decreasing df reading 62, symptoms of Stage B are indicated if the next reading is an increase in df as shown by reading 64; however, if the next reading after the two successive decreasing readings 60, 62 is a third decrease, a false ovulation stage is likely and a "safe period" is indicated whereby the analysis with the next reading returns to that of the "safe period" and testing for Stage A. Stage B occurs approximately 2 days prior to ovulation. It is again noted that Stage B may be indicated for more than 1 day of readings due to variations in the menstrual cycle.

Once Stage B is indicated, up to 2additional succeeding increases in df, 66 and 68, may be recorded indicating Stage B each time. If a third successive increase in df occurs after 68, a likely false stage ovulation and a "safe period" is indicated. In this event, the next df reading will be analyzed in accordance with the "safe period" criteria and status described above.

While the subject is in Stage B, a decrease in df after any of the readings 64, 66, 68 indicates that Stage C has been entered as shown by reading 70. Stage C corresponds approximately to one day prior to ovulation. Once Stage C is indicated, a second successive decrease in df 72 should follow, again indicating Stage C. If, however, the next reading after the first Stage C indication 70 is an increase in df, a false ovulation stage is signified and a "safe period" indicated. The analysis then proceeds in accordance with the "safe period" status previously described.

After the second decreasing df 72 in Stage C, the next reading 74 is an increase in df indicating that Stage D has been reached, and that the subject has approximately reached the time of ovulation; however, if the next reading after the second Stage C reading 72 is a decrease in df, not an increase as in reading 74, a false ovulation stage is indicated, a "safe period" is displayed, and the analysis then continues in accordance with the "safe period" status previously described.

Once Stage D is reached, the next reading of df, 76, whether increasing or decreasing, indicates a completed ovulation cycle. A "safe" period begins with the next reading 78 the analysis of the data is repeated as described, analyzing the df measurement data for Stage A.

As other or improved models of the ovulation cycles are developed, modifications of the above analysis and program can be made without departing from the spirit or scope of the invention disclosed. Thus, it is seen that the measurement and comparison of data corresponding to the frequency change, df, in accordance with the invention can be used to predict the onset of ovulation, which can be used to aid conception, and also as a birth control tool to avoid conception. Once Stage A is entered (approximately 3 days to ovulation), the likelihood of ovulation is increased, with ovulation finally being indicated in Stage D. Data corresponding to the safe period indicates when conception is not probable.

Figure 8:
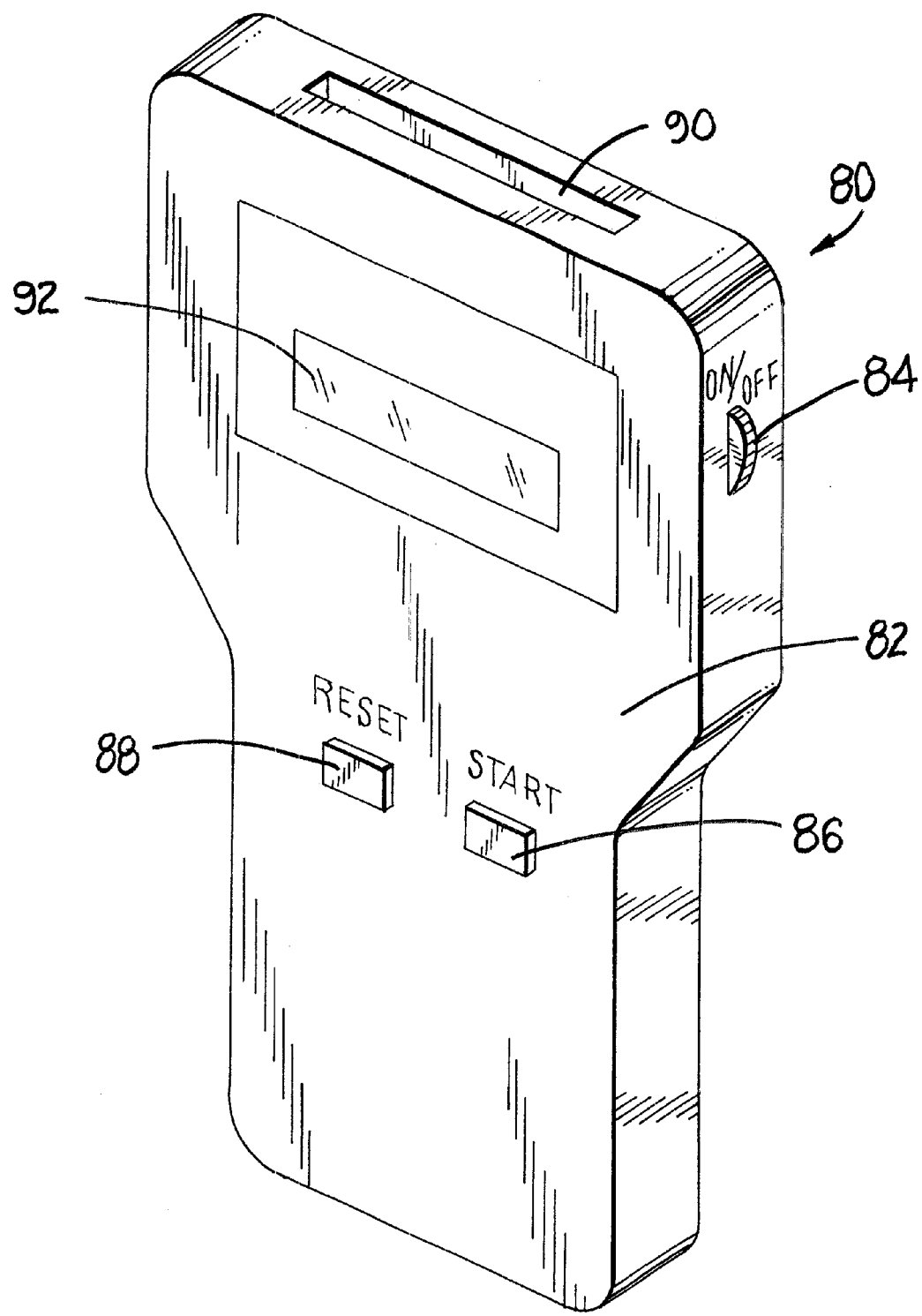
FIG. 8 is a front perspective view of one embodiment of a portable handheld device for practicing the invention.

Referring now to FIG. 8, an apparatus 80 for carrying out the measurement and calculation of df data and analyzing the data in accordance with the above method includes a housing 82 for the apparatus having an on/off switch 84, a start switch 86, a reset switch 88 and a display panel 92. At one end of the device, an opening 90 containing an internal connector (not shown) for receiving the frame 60 containing oral sensor 20 in electrical contact with the internal electrical circuit.

Figure 9:
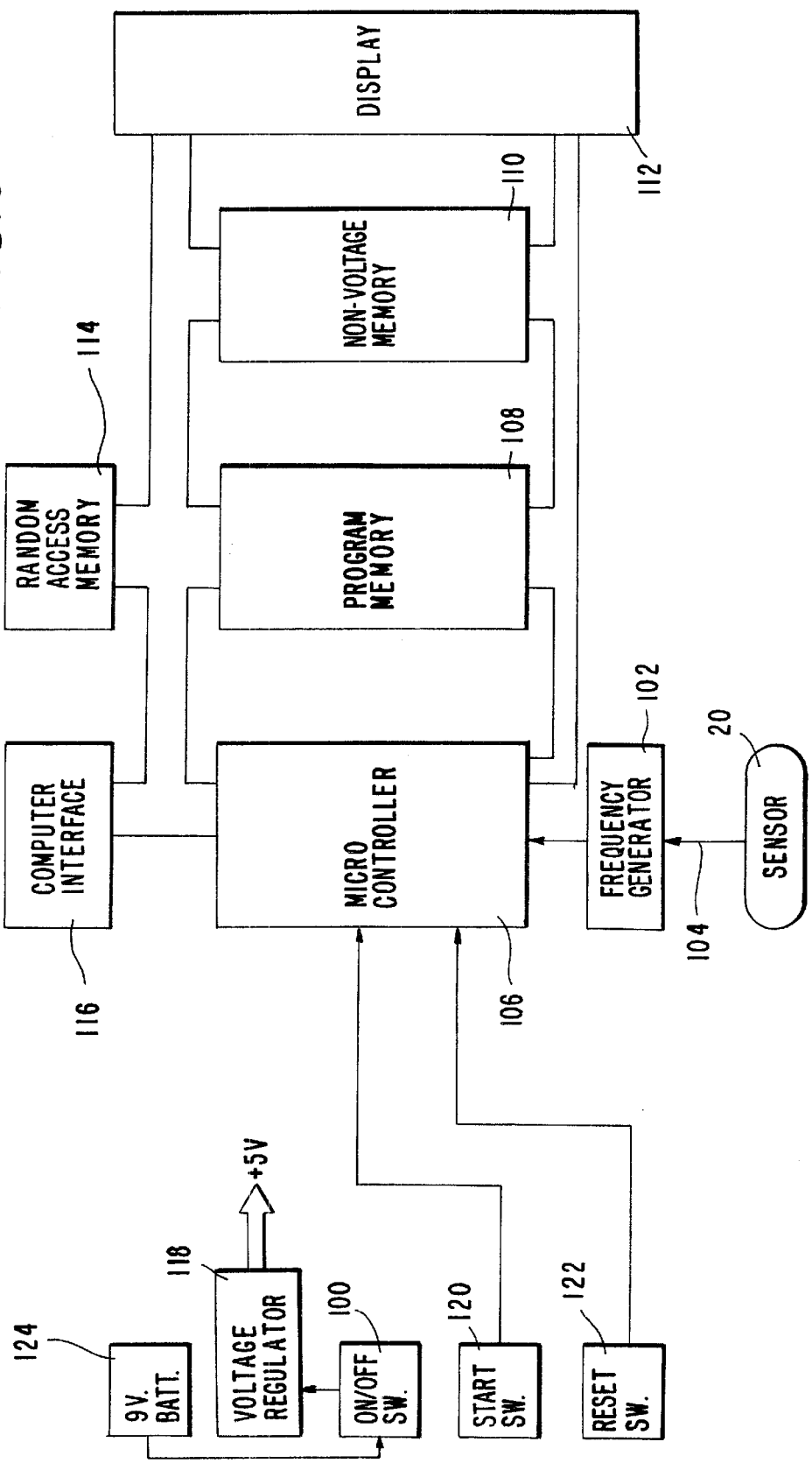
FIG. 9 is a block circuit flow diagram of a preferred embodiment for the practice of the invention.

An electrical schematic diagram of the device is illustrated in FIG. 9. In this embodiment, a digital processor 106 carries out the entire process. The processor comprises on/off power switch 100, a frequency generating oscillator 102, a socket or connection point 104 for the oral sensor 20, a micro-controller chip 106 for controlling the entire diagnostic process, program memory 108 for filtering data, non-volatile memory 110 for storage, a display screen 112, random access memory 114, computer interface 116, voltage regulator 118, start switch 120, reset switch 122 and battery 124. A suitable micro-controller 106 for use in the practice of the invention is Intel model 80c196, or an equivalent.

Figure 10:
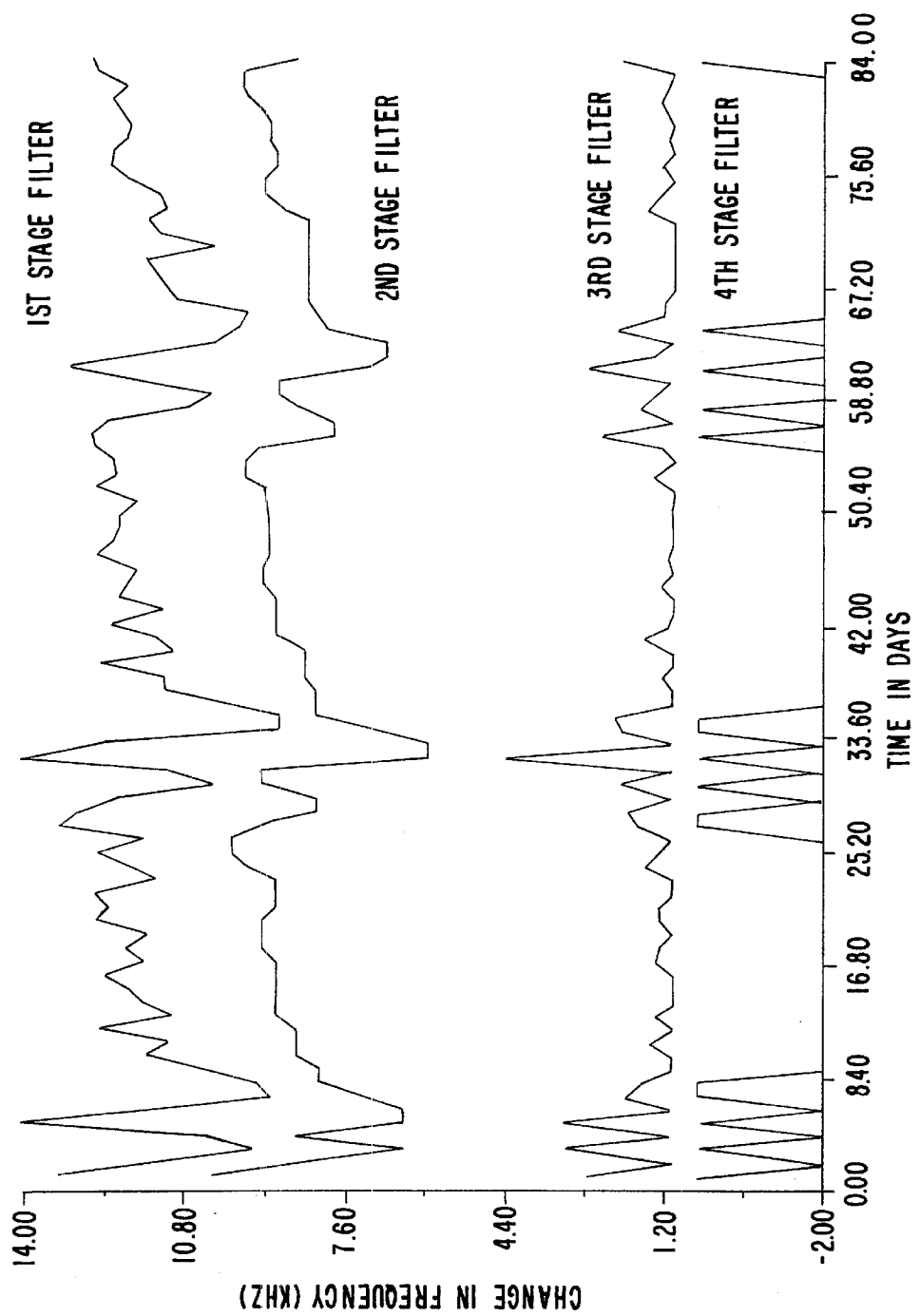
FIG. 10 is a diagram illustrating one preferred embodiment for the signal filter processing utilized in the practice of the invention.

In addition to carrying out the measurement and calculation of df and providing an indication of the menstrual cycle stages and ovulation as previously explained, the apparatus can also store data for future retrieval through the interface 116. The processor 106 is programmed to filter the df readings as shown in FIG. 10, in four stages so that the various stages of ovulation are represented by peaks, i.e., in the fourth stage, which data is easily stored in long term memory and which can be retrieved, if desired, for purposes of analysis, statistical studies, research, and the like.

To use the apparatus of FIGS. 8 and 9, a fresh unused oral sensor 20, is inserted into the apparatus to connect to the internal circuit. The device is turned on and the oral sensor 20 is placed into the mouth, preferably under the tongue as previously described. The start button 120 is pressed, initiating the process of taking a frequency reading, analyzing the data as described above, and displaying an indication of the subject's stage in the menstrual cycle. The display can indicate whether the subject is in the "safe period", 3 days to ovulation, 2 days to ovulation, or the like in accordance with the program's analysis of the data.

It should also be understood that the device can be provided with an audible signal means and an appropriate program to provide a simulated voice output corresponding to the visual display screen described above. The voice simulation mode can be utilized by subjects having vision impairments and can be an optional mode controlled by the subject, for use separately or simultaneously with the visual display means. From the above, it will be understood that, as used herein, "data display means" includes visual and audible signal indicia by which information concerning the subject's fertility status is communicated, and also includes a monitor or printer on which such information is portrayed in graphic, tabular or text form.

When the device is new or when a new subject first begins to use the device, the first cycle is required to establish the baseline or reference frequency to be used in determining df for that subject. Since the data stored is specific for each subject, a new subject must reset the apparatus by pressing reset switch 122 to clear the memory of data specific to the previous subject before utilizing the device.

Figure 11:
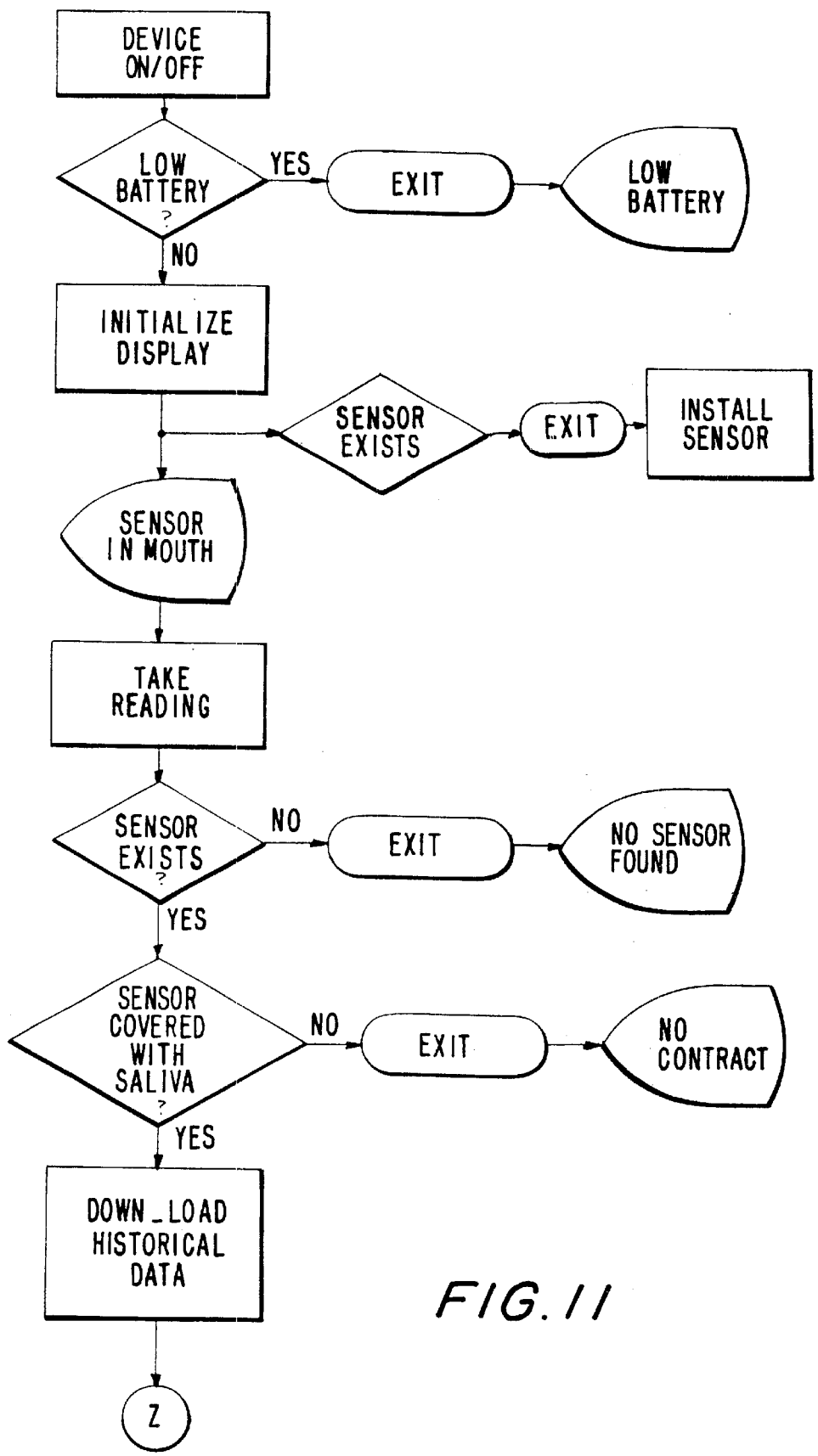
FIG. 11 is a process flow diagram illustrating the application of a preferred embodiment of the method and apparatus of the invention to the step of measuring frequency.
Figure 12:
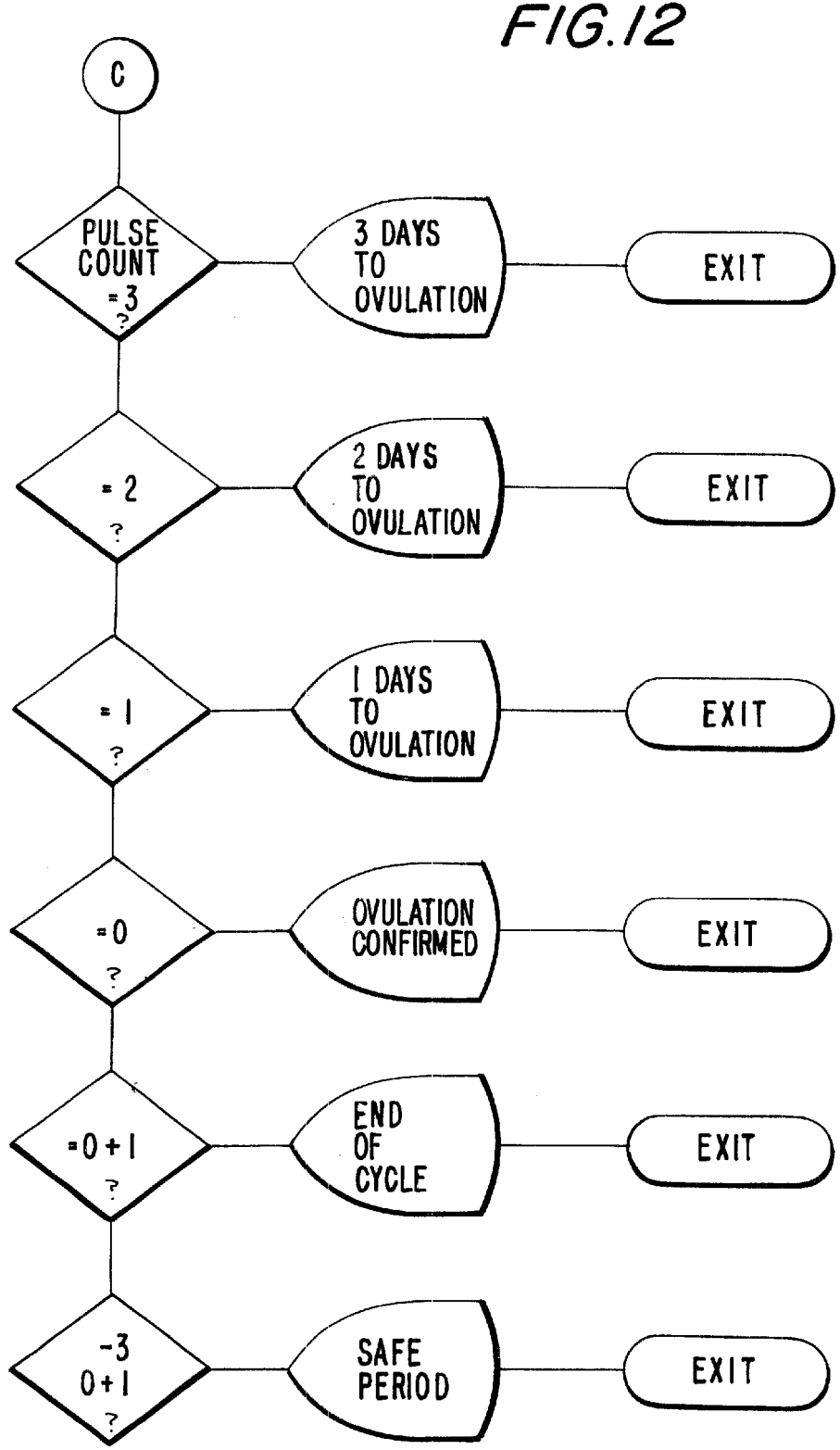
FIG. 12 is a process flow diagram illustrating an embodiment display sequence based on measurements.

A logic circuit for use in connection with the method of the invention will be described with reference to FIGS. 11 through 15. It is to be understood that the instructions to the subject or status information can be visually displayed on a screen provided for that purpose and/or communicated audibly by simulated or synthesized voice signals. Referring to FIG. 11, the start-up routine commences with a battery check when the on switch is activated, followed by a circuit integrity check to confirm that a sensor has been installed in the oscillator circuit. An optional display can include an inquiry or reminder concerning the need to use a fresh or new oral sensor. After the subject places the oral sensor in her mouth and activates the start switch, a series of frequency reading samplings is initiated by the programmed microprocessor until a stable frequency is recognized; in the absence of a frequency reading, a "re-install sensor" message can be transmitted. Once a stable frequency has been detected within the prescribed time period, which can be 20 seconds, the data is recorded in the memory device.

It should also be understood that multiple registers can be established by assigning each subject a personal identification number ("PIN") of other unique indicia which must be entered before use in order to access that subject's personal data storage file. A lock-out feature can be provided so that the PIN must be entered after a specified period of time, after an oral sensor has been removed from the device or when a new oral sensor is installed in the circuit. In an especially preferred embodiment, a subject is provided with a plurality of sensors, each of which is electronically personalized and encoded, which code is recognized and recorded upon each installation of a fresh sensor into the device. Alternatively, each sensor can be provided with a personalized bar code and the device provided with a scanner;. in a preferred aspect of this embodiment, the bar code on the oral sensor must be scanned prior to its introduction into the circuit in order to proceed further. Other methods and means for separating multiple subject's data in a single device will be apparent to those of ordinary skill in the art from the above examples. The program logic is further described with reference to FIG. 12 in which the change in frequency data is compared to the subject's personal baseline data. The starting point "C" proceeds from the program logic illustrated in FIG. 15, and which is described in detail below. After a given day's measurement and change in frequency calculation, a comparison is made to the subject's historic data of the previous days' data for purposes of determining the value of the pulse counts. Each of these determinations corresponds to a signal display that is communicated to the subject, after which the program is exited. The circuit can be provided with an automatic deactivation of the display screen and/or a time-delayed automatic shut-off in order to minimize the power drain on the battery.

Figure 13:
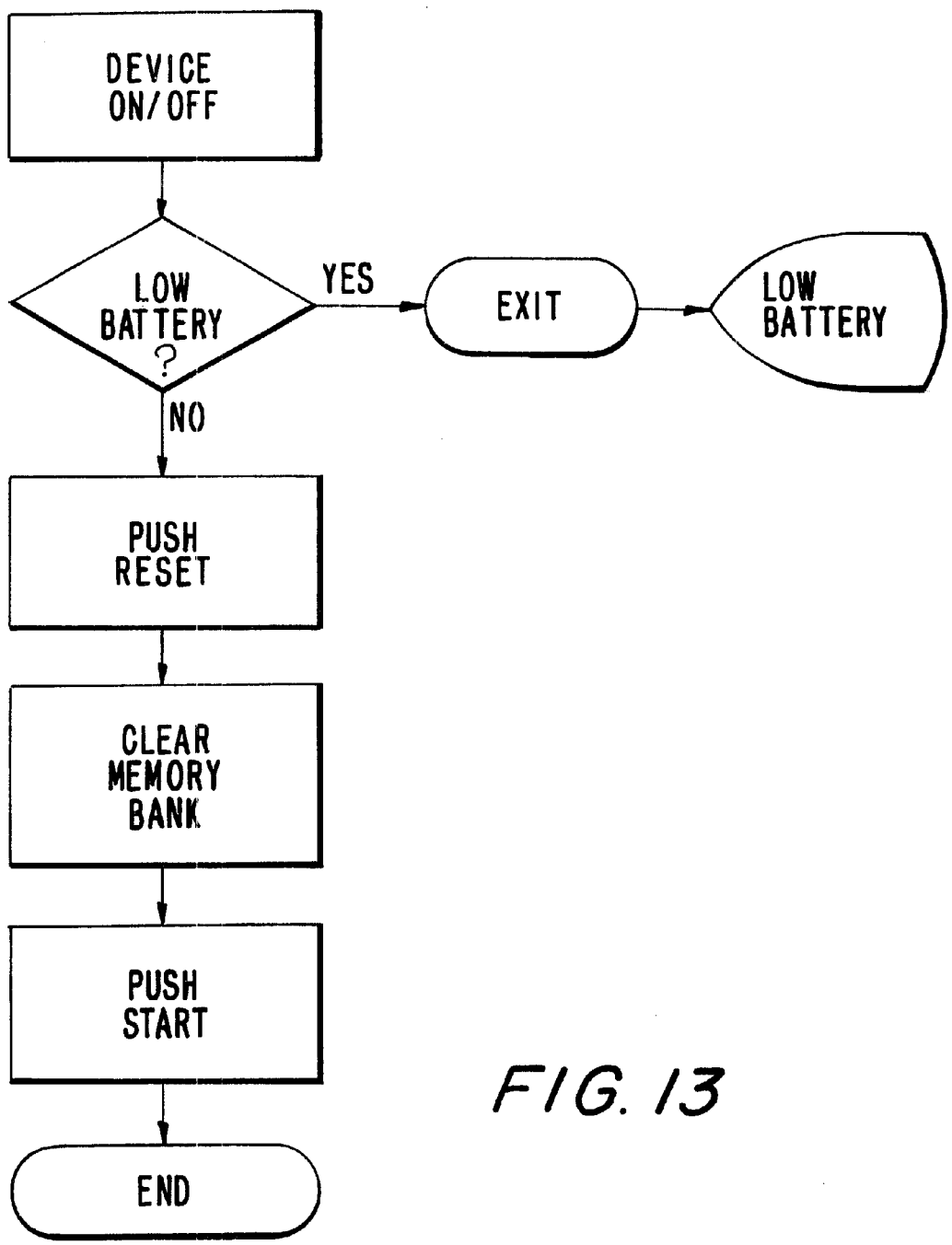
FIG. 13 is a process flow diagram illustrating one embodiment of the reset function.

The reset circuit program logic is illustrated in FIG. 13 and is used in the event a new subject is to use the apparatus, or the same subject has inadvertently failed to take the appropriate daily measurements so that the accumulated data is not appropriate for the analytical and predictive purposes of the invention. It will also be understood that the reset program can be established to maintain a successful personal historic baseline for a given subject, and this data will be maintained in the memory device even if the reset function is activated during a given subsequent cycle.

Figure 14:
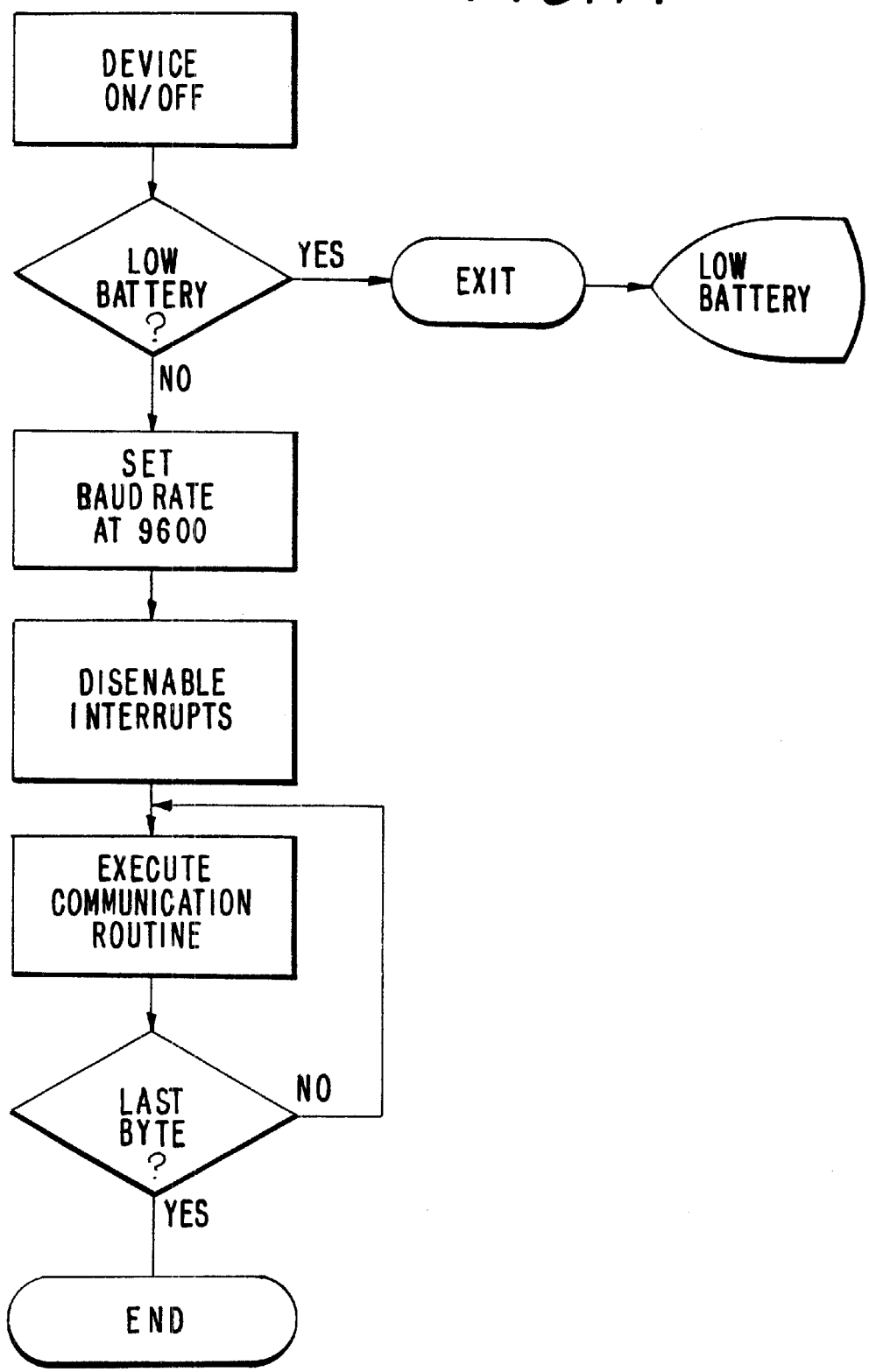
FIG. 14 is a process flow diagram illustrating one embodiment of the computer interface function.

The computer interface program logic is illustrated in FIG. 14 for one preferred embodiment. Following a routine battery power check, which is common to all of the programs, the desired BAUD rate is set and the program proceeds as indicated. Note that a check is also made to confirm the availability of adequate memory as part of the program routine.

Figure 15:
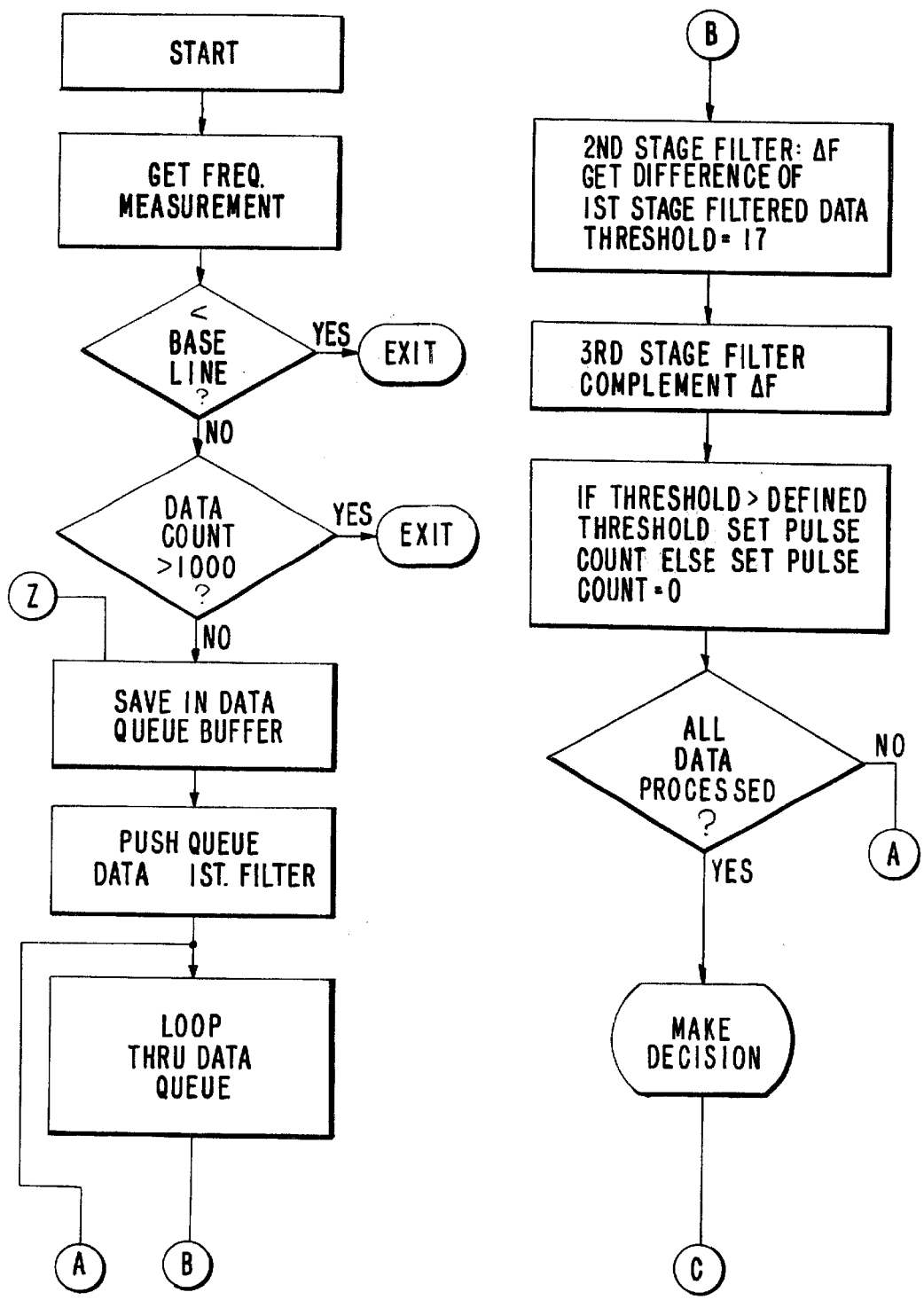
FIG. 15 is a process flow diagram illustrating one embodiment for the processing of an incoming measured frequency signal.

The complete program logic for processing incoming oral sensor frequency signal measurements is illustrated in the flow diagram of FIG. 15. The sub-routines in A, C and Z described above are identified at their appropriate positions in the logic circuit. The processing of the data through the multi-stage filters is indicated, as well as the initial comparison of the frequency measurement with the baseline data. Once the appropriate data processing steps have been completed, the program enters sub-routine C and the display is transmitted for viewing by the subject as described above in connection with FIG. 12.

From the above it is apparent that the present invention provides a simple and inexpensive method and apparatus for diagnosing the menstrual and ovulation cycle of a female.

The invention provides a reliable means of self-monitoring for use in the home. It also provides a means for physicians to monitor the subject female.

I claim:
1. A method for determining the onset of ovulation in a female subject comprising:
   a. providing an oral sensor;
   b. connecting the oral sensor to an electrical circuit comprising:
      (i) frequency generating oscillator means;
      (ii) frequency measurement means;
      (iii) data processing and control means;
      (iv) data storage means; and
      (v) data display means;
   c. contacting the oral sensor on a first day with the subject's saliva until a stable frequency is indicated by the frequency measurement means;
   d. recording the first day's frequency measurement;
   e. repeating steps (c) and (d) on a subsequent day to obtain a second frequency measurement;
   f. calculating the difference in frequency, df, between the first and the second day's frequencies;
   g. recording the df calculated in step (f);
   h. repeating steps (e) through (g) on each successive day of the subject's menstrual cycle to establish an historic baseline of the df value for each of the days;
   i. applying the baseline df values to an algorithm corresponding to predetermined patterns of df values for menstrual cycles;
   j. recording the baseline data from step (i) in the data storage means corresponding to the subject's historical menstrual cycle;
   k. repeating steps (c) through (h) for each day in a subsequent menstrual cycle of the same subject and recording the data in the data storage means in association with the subsequent cycle;
   l. comparing the data obtained in step (k) with the data obtained in step (j) to determine the subject's fertility state; and
   m. displaying data from the data storage means on the data display means corresponding to the subject's fertility state in the menstrual cycle.

2. The method of claim 1 where the data is displayed in step (m) daily.

3. The method of claim 1 where a new oral sensor is connected to the circuit for each frequency measurement.

4. The method of claim 1 which includes the step of removing the oral sensor after each frequency measurement and replacing it with a new oral sensor.

5. The method of claim 1 where the oral sensor is connected to the electrical circuit by manually inserting one end of the oral sensor into a female socket.

6. The method of claim 1 where the oral sensor is connected to the electrical circuit by securing the oral sensor in a spring contact.

7. The method of claim 1 where the oral sensor includes a non-conducting supporting frame.

8. The method of claim 1 which further includes the steps of
   a. measuring the frequency of the circuit after the oral sensor is connected to the circuit;
   b. comparing the measured frequency to a predetermined frequency or frequency range; and
   c. generating a signal corresponding to the condition of oral sensor.

9. The method of claim 1 which includes the further step of processing the df data utilizing at least one algorithm contained in the data processing and control means.

10. An oral sensor for use in an oscillator circuit, the oral sensor comprising a laminated article formed from:
   a. an electrically conductive first layer;
   b. a non-conductive second layer;
   c. an electrically conductive third layer;
   d. a non-conductive fourth layer; and
   e. an electrically conductive fifth layer,
where the third and fourth layers are perforated and the third and fifth layers are in electrical contact with each other through the perforations in the fourth layer, and the second and fourth layers contact each other through the perforations in the third layer.

11. The oral sensor of claim 10 where the first and fifth layers of the laminated structure are leads to the oscillator circuit.

12. The oral sensor of claim 10 where the electrically conductive layers are aluminum.

13. The oral sensor of claim 12 where the aluminum has a purity of about 99.9%.

14. The oral sensor of claim 12 where the thickness of each of the aluminum layers is about 0.02 mm.

15. The oral sensor of claim 10 where the non-conductive layers are formed from polymeric material.

16. The oral sensor of claim 15 where the polymeric material is polyethylene terephthalate.

17. The oral sensor of claim 10 where each of the non-conductive layers are formed from the same dielectric material.

18. The oral sensor of claim 16 where the thickness of each of the non-conductive layers is about 0.02 mm.

19. The oral sensor of claim 10 where the perforations in the layers constitute about five percent of the total area of the layer.

20. The oral sensor of claim 10 where the layers are of uniform size and are received in a resilient supporting frame.

21. The oral sensor of claim 20 where the supporting frame extends along the margins of two sides and a proximal end of the laminated structure and includes a cross-member proximate the distal end of the laminated structure.

22. The oral sensor of claim 21 where the distal end portion of the laminated structure extending from the cross-member of the frame comprise electrical leads.

23. The oral sensor of claim 22 where the electrical leads are metal-plated to improved their electrical conductivity.

24. The oral sensor of claim 10 where the layers are bonded together under heat and pressure.

25. The oral sensor of claim 22 where the electrical leads are configured to engage a spring contact in the oscillator circuit.

26. The oral sensor of claim 10 which further comprises a surrounding hermetically sealed wrapper.

27. The oral sensor of claim 26 in which the distal end of the wrapper is defined by release means, whereby the proximal end of the wrapper remains on the proximal end of the sensor when the distal end of the wrapper is removed.

28. The oral sensor of claim 26 where the proximal end of the wrapper extends from about the cross member to the proximal end of the sensor.

29. The oral sensor of claim 26 where the wrapper is sterilizable.

30. A method of monitoring the menstrual cycle in a female mammal subject comprising:
   a. providing a capacitive oral sensor;
   b. contacting the capacitive oral sensor with the mammal's saliva on a daily basis;
   c. measuring a change in frequency associated with the oral sensor during step (b);
   d. calculating any change in frequency between each subsequent daily measurement and the previous day's measurement; and
   e. utilizing the calculated daily changes in frequency to predict ovulation during the subject's menstrual cycle.

31. The method of claim 30 wherein said change in frequency is in an oscillator circuit in which said oral sensor is a component and wherein employing said measurement comprises the step of comparing said measurement with a previous measurement.

32. The method of claim 31 where the mammal is a human.

33. A method of diagnosing the onset of the fertile period of a female mammal subject comprising:
   a. monitoring the concentration of electrolytes in solution by measuring changes in capacitance/permeability of a capacitive oral sensor that is in contact with said bodily fluid; and
   b. providing an indicator for responding to the changes in capacitance of said capacitive oral sensor, whereby the response of said indicator is diagnostic of the onset of the fertile period of said female.

34. A capacitive oral sensor comprising:
   a. a non-conductive element separating first and second conducting elements to form a capacitor-like component; and
   b. terminals associated with said capacitor-like element connectable to an electric circuit that is responsive to the capacitance of said oral sensor, wherein the capacitance of said oral sensor varies as a function of the concentration of electrolytes which contact the oral sensor.

35. An apparatus for monitoring the changes of electrolyte concentration in a liquid medium comprising:
   a. an oral sensor introducible into the medium, said oral sensor's capacitance varying with the concentration of electrolyte;
   b. means for detecting any changes in the capacitance of said oral sensor; and
   c. means for indicating the result of said change in capacitance.

36. A diagnostic system for determining the onset of ovulation in a female subject, comprising;
   a. a digital processor;
   b. a capacitive oral sensor;
   c. a connector for electrically connecting the oral sensor to said processor, said oral sensor causing a change in frequency response when in contact with an electrolyte; and
   d. a display for indicating the onset of ovulation.

37. The diagnostic system of claim 36 which further includes an oscillator circuit, whereby the frequency response of the circuit varies when the oral sensor is contacted with an electrolyte.

38. The diagnostic system of claim 37 where the oral sensor is comprised of a laminated article formed from:
   a. an electrically conductive first layer;
   b. a non-conductive second layer;
   c. an electrically conductive third layer;
   d. a non-conductive fourth layer; and e. an electrically conductive fifth layer, where the third and fourth layers are perforated and the third and fifth layers are in electrical contact with each other through the perforations in the fourth layer, and the second and fourth layers contact each other through the perforations in the third layer.

39. A method of predicting ovulation in a female human subject, which subject has experienced the onset of menstruation in her fertility cycle, the method comprising:

a. providing a first capacitive oral sensor;

b. providing an oscillator circuit having a known frequency characteristic;

c. incorporating the first oral sensor in the oscillator circuit;

d. measuring on a first test day a first frequency of the oscillator circuit that incorporates the oral sensor;

e. recording the first frequency;

f. contacting the capacitive oral sensor with subject's saliva for a period of time that is sufficient to obtain a stable second frequency response in the oscillator circuit;

g. recording the second frequency;

h. calculating the value and direction of the change in frequency between the first and second recorded frequencies;

i. recording the results of step (h) as df;

j. removing the first capacitative oral sensor from the oscillator circuit;

k. providing a second unused capacitive oral sensor;

l. incorporating the second oral sensor in the oscillator circuit;

m. repeating steps (d) through (i) above, on a second and subsequent test days 3 through n, where n is the total number of days in the subject's menstrual cycle, and recording the results in step (i) as $(df)_2$ through $(df)_n$; and repeating steps (j) through (l) after the second and subsequent test days; and n. providing and indication of the onset of ovulation as a function of the maximum value of an increase in the change of frequency following the onset of menstruation, which maximum increase in the change of frequency is followed by a nadir and subsequent sharp increase in the rate of change in frequency.

40. The method of claim 39 where the indication provided in step (n) is selected from the group consisting of a visual indicia and an audible signal.

41. The method of claim 38 where the indication is a visual indicia selected from the group consisting of text, graphic display, tabular display and combinations thereof.

* * * * *